United States Patent [19]

Been et al.

[11] Patent Number: 5,712,128
[45] Date of Patent: Jan. 27, 1998

[54] ENZYMATIC RNA MOLECULES

[75] Inventors: Michael D. Been; Sarah P. Rosenstein, both of Durham; Anne T. Perrotta, Garner, all of N.C.

[73] Assignee: Duke University, Durham, N.C.

[21] Appl. No.: 434,453

[22] Filed: May 3, 1995

Related U.S. Application Data

[62] Division of Ser. No. 238,963, May 5, 1994, which is a continuation of Ser. No. 821,155, Jan. 13, 1992, abandoned.

[51] Int. Cl.$^6$ .................. C12P 19/34; A61K 48/00; C12N 15/11; C07H 21/04
[52] U.S. Cl. .................. 435/91.31; 514/44; 536/23.1; 536/24.5
[58] Field of Search .................. 435/91.1, 91.31, 435/91.4; 514/44; 536/23.1, 24.5

[56] References Cited

U.S. PATENT DOCUMENTS

| | | | |
|---|---|---|---|
| 4,987,071 | 1/1991 | Cech et al. | 435/91 |
| 5,225,337 | 7/1993 | Robertson et al. | 435/91 |
| 5,225,347 | 7/1993 | Golberg et al. | 435/320.1 |

FOREIGN PATENT DOCUMENTS

| | | |
|---|---|---|
| 9104319 | 4/1991 | WIPO. |
| 9104324 | 4/1991 | WIPO. |
| 9219732 | 11/1992 | WIPO. |
| 9305157 | 3/1993 | WIPO. |

OTHER PUBLICATIONS

Sullivan et al., Reversibility of cyclization of the Tetrahymena rRNA intervening sequence: Implication for the mechanism of splice site choice, Cell v. 42, pp.639–648, Sep. 1985.
Cech, The generality of self-splicing RNA: relationship to nuclear mRNA splicing, Cell, v. 44 pp. 207–210 Jan. 1986.
Perrault et al., Mixed deoxyribo-and ribo-oligonucleotides with catalytic activity, Nature, v. 344 pp. 565–567, May 1990.
Christoffersen et al., Ribozymes as human therapeutic agents, Journal of Medicinal Chemistry, v. 36 pp. 2023–2037, 1995.
Stull et al., Antigene, ribozyme and aptomer nucleic acid drugs: progress and prospects, Pharmaceutical Research, v. 12 (4) pp. 465–483, 1995.
Sullivan et al. Reversibility of cyclization of the tetrahymena rRNA intervening sequence: implication for the mechanism of splice site choice, Cell, vol. 42, pp. 639–648, Sep. 1985.
Belinsky and Dinter–Gottlieb, "Characterizing the Self–Cleavage of a 135 Nucleotide Ribozyme from Genomic Hepatitis Delta Virus," *The Hepatitis Delta Virus*, Wiley-Liss, Inc., pp. 265–274 (1991).
Branch and Robertson, "Efficient trans cleavage and a common structural motif for the ribozymes of the human hepatitis δ agent," *Proc. Natl. Acad. Sci. USA* 88:10163–10167 (1991).
Harland et al., *Development* 102:837–852 (1988).
Kunkel et al., "Rapid and Efficient Site–Specific Mutagenesis without Phenotypic Selection," *Methods Enzymol.* 154:367–382 (1987).
Kuo et al., "Characterization of Self–Cleaving RNA Sequences on the Genome and Antigenome of Human Hepatitis Delta Virus," *J. Virology* 62:4439–4444 (1988).
Maniatis et al., *Nature* 325:673–698 (1987).
Perrotta and Been, "A pseudoknot–like structure required for efficeint self–cleavage of hepatitis delta virus RNA," *Nature* 350:434–436 (1991).
Perrotta and Been, "Cleavage of Oligoribonucleotides by a Ribozyme Derived from the Hepatitis δ Virus RNA Sequence," *Biochemistry* 31:16–21 (1992).
Perrotta and Been, "The self–cleaving domain from the genomic RNA of hepatitis delta virus: sequencerequirements and the effects of denaturant," *Nucleic Acids Research* 18:6281–6827 (1990).
Rosenstein and Been, "Evidence that genomic and antigenomic RNA self–cleaving elements from heptatis delta virus have similar secondary structures," *Nucleic Acids Research* 19:5409–5416 (1991).
Rosenstein and Been, *Biochemistry* 29:8011 (1990).
Sharmeen et al., "Antigenomic RNA of Human Hepatitis Delta Virus Can Undergo Self–Cleavage", *J. of Virology*, 62:2674–2679 (1988).
Sullivan and Cech, "Reversibility of Cyclization of the Tetrahymena rRNA Intervening Sequence: Implication for the Mechanism of Splice Site Choice", *Cell*, vol. 42, 639–648, 1985.
Symons, "Self–cleavage of RNA in the replication ofsmall pathogens of plants and animals," *TIBS* 14:445–450 (1989).
Szostak, "Enzymatic Activity of the Conserved Core of a Group I Self–Splicing Intron," *Nature* 322:83–86 (1986).
Taira et al., "Construction of a novel artificial–ribozyme–releasing plasmid," *Protein Engineering* 3:733 (1990).
Taira et al., "Construction of a novel RNA–transcript–trimming plasmid which can be used both in vitro in place of run–off and (G)–free transcriptions and in vivo as multi–sequences transcription vectors," *Nucleic Acids Research* 19:5125 (1991).
Thill et al., "Self–clevage of a 71 nucleotide–long riobzyme derived from hepatitis delta virus genomic RNA", *Nucleic Acids Research*, 19:6519–6525 (1991).
Vieira and Messing, "Production of Single–Stranded Plasmid DNA," *Methods in Enzymol.* 153:3–11 (1987).
Wu et al., "Human hepatitis δ virus RNA subfragments contain an autocleavage activity," *Proc. Natl. Acad. Sci. USA* 86:1831–1835 (1989).

*Primary Examiner*—George C. Elliott
*Assistant Examiner*—Andrew Wang
*Attorney, Agent, or Firm*—Lyon & Lyon LLP

[57] ABSTRACT

Nucleic acid molecule having an RNA substrate cleaving enzymatic activity which cleaves a separate RNA substrate at a cleavage site. The nucleic acid molecule includes an RNA substrate binding portion which base pairs with the RNA substrate only 3' of the cleavage site, and an enzymatic portion (which may include a part or all of the RNA substrate binding portion) having the enzymatic activity. The nucleic acid molecule is able to base pair with the RNA substrate only 3' of the cleavage site, and cause cleavage of the RNA substrate at that cleavage site. The nucleic acid molecule can be either linear or circular. A general method for forming circular RNA in vivo and in vitro is provided.

5 Claims, 16 Drawing Sheets

FIG. 1g.

ANTIGENOMIC

CIRCULAR RNA

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
( A ) LENGTH: 11 base pairs
( B ) TYPE: nucleic acid
( C ) STRANDEDNESS: single
( D ) TOPOLOGY: linear ( x i ) SEQUENCE DESCRIPTION: SEQ ID NO:1:

UUCGGGUCGG C     11

( 2 ) INFORMATION FOR SEQ ID NO:2:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear ( x i ) SEQUENCE DESCRIPTION: SEQ ID NO:2:

UUCGGGUCGG CAU     13

( 2 ) INFORMATION FOR SEQ ID NO:3:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( x i ) SEQUENCE DESCRIPTION: SEQ ID NO:3:

UUCGGGUCGG     10

( 2 ) INFORMATION FOR SEQ ID NO:4:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear ( x i ) SEQUENCE DESCRIPTION: SEQ ID NO:4:

UUCGGCACGG CAU     13

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
AGGAGGTGGA GATGCCCTAT AGTGAGTCGT                                    30
```

( 2 ) INFORMATION FOR SEQ ID NO:6:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

```
UUCGGGUCGG CAUGGCAUCU CCACCUCCUC GCGGUCCGAC CUGGGCAUCC              50
GAAGGAGGAC GUCGUCCACU CGGAUGGCUA AGGGAG                             86
```

( 2 ) INFORMATION FOR SEQ ID NO:7:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

```
UUCGGGUCGG CAU                                                      13
```

( 2 ) INFORMATION FOR SEQ ID NO:8:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
GGGCAUCCGA CCUGGGCAAG CU                                            22
```

( 2 ) INFORMATION FOR SEQ ID NO:9:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
UUCGGCACGG CAU                                                      13
```

( 2 ) INFORMATION FOR SEQ ID NO:10:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
GGGCAUCCGU GCUGGGCAAG CU                                            22
```

( 2 ) INFORMATION FOR SEQ ID NO:11:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
UGGCCGGCAU  GGUCCCAGCC  UCCUCGCUGG  CGCCGGCUGG  GCAACAUUCC      50

GAGGGGACCG  UCCCCUCGGU  AAUGGCGAAU  GGGAC                       85
```

( 2 ) INFORMATION FOR SEQ ID NO:12:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "S" stands for
            for C or G. The letter
            "W" stands for U or A.

( x i ) SEQUENCE DESCRIPTION: SEQ ID NO:12:

```
CGGSWCGGCA  UGGCAUCWSC  ACCUCCUCGC  GGUCCGWSCU  GGGCAUCCGA      50

AGGAGGACGC  ACGUCCACUC  GGAUGGCUAA  GGSWG                       85
```

( 2 ) INFORMATION FOR SEQ ID NO:13:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
CGGGUCGGCA  UGGCAUCUCC  ACCUCCUCGC  GGUCCGACCU  GGGCAUCCGA      50

AGGAGGACGU  CGUCCACUCG  GAUGGCUAAG  GGAG                        84
```

( 2 ) INFORMATION FOR SEQ ID NO:14:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for
            any base.

( x i ) SEQUENCE DESCRIPTION: SEQ ID NO:14:

```
NGGGUCGGCA  UGGCAUCUCC  ACCUCCUCGC  GGUCCGACCU  GGGCAUCCGA      50

AGGAGGACGU  CGUCCACUCG  GAUGGCUAAG  GGAG                        84
```

( 2 ) INFORMATION FOR SEQ ID NO:15:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:

( D ) OTHER INFORMATION: The letter "K" stands for
for G or U. The letter
" R" stands for G or A.
The letter "S" stands for
G or C.

( x i ) SEQUENCE DESCRIPTION: SEQ ID NO:15:

CGGGUCGGCA UGGCAUCUCC ACCUCCUCGC GGUCCGACCU KRSKRSKRSC  50

AUCUUCGGAU GGCUAAGGGA G  71

( 2 ) INFORMATION FOR SEQ ID NO:16:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GGGCAUCUCC ACCUCCUCGC GGUCCGACCU GGGCAUCCGA AGGAGGACGA  50

CGUCCACUCG GAUGGCUAAG GGAGCAAGCU  80

( 2 ) INFORMATION FOR SEQ ID NO:17:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

UUCGGGUCGG CAU  13

( 2 ) INFORMATION FOR SEQ ID NO:18:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

GGGCAUCUCC ACCUCCUCGC GGUCCGACCU GGGCAUCUUC GGAUGGCUAA  50

GGGAGCAAGC U  61

( 2 ) INFORMATION FOR SEQ ID NO:19:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

GGUCCAGCCU CCUCGCGGCC CGACCUGGGC AUCUUCGGAU GGCGAAUGGA UC  52

( 2 ) INFORMATION FOR SEQ ID NO:20:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

GGGAAUUCGA UGGCGAAUGG CUUCGGCCAG CCUCCUCGCG GCCCGACCUG  50

GGCAUCGGAU C                                                                                            6 1

( 2 ) INFORMATION FOR SEQ ID NO:21:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

GGGCAUCUUC GGAUGGCGAA UGGCUUCGGC CAGCCUCCUC GCGGC                                                       4 5

ENZYMATIC RNA MOLECULES

This is a division of application Ser. No. 08/238,963, filed May 5, 1994, which is a continuation of application Ser. No. 07/821,155, filed Jan. 13, 1992, now abandoned hereby incorporated by reference herein in totality, including drawings.

This invention relates to enzymatic RNA molecules, sometimes termed ribozymes, able to cleave other RNA molecules. The U.S. government may have rights in the invention which was made in part with support from the N.I.H. (GM-40689).

BACKGROUND OF THE INVENTION

Cech et al., U.S. Pat. No. 4,987,071, describe various RNA molecules which have one or more enzymatic activities, e.g., an endoribonuclease activity which acts to cleave other RNA molecules. Such activity is termed intermolecular cleaving activity. These enzymatic RNA molecules are derived from an RNA molecule which has an activity which results in its own cleavage and splicing. Such self-cleavage is an example of an intramolecular cleaving activity.

Perrotta and Been, 18 *Nucleic Acids Research* 6821, 1990, describe a self-cleaving domain from the genomic RNA of hepatitis delta virus (HDV). They describe the minimal sequence required for cleavage at the self-cleavage site of the HDV genomic strand, and present evidence that sequences that fall outside of this domain can inhibit the cleavage reaction. They state:

> It has often been possible with other self-cleaving and self-splicing RNAs to physically separate the 'ribozyme' into enzyme and substrate portions. For HDV self-cleaving RNA, similarly successful separations may be possible. If the single nucleotide required 5' to the break site is viewed as part of the substrate, then the remainder of the substrate and the entire catalytic portion must reside in the sequence 3' of the break site. Our results indicate that, for self-cleavage of the HDV genomic RNA, significant interactions with 'substrate' sequence 5' to the site of cleavage may be limited to the uridine at the break site. Although the requirement for a longer sequence might be anticipated, self-cleavage of the vLTSV RNA requires only 3 nt 5' to the break site and there is precedent for even shorter sequences flanking the sites of cleavage in other RNA catalyzed reactions. For example, a ribozyme derived from the Tetrahymena group I intron catalyzes the cleavage of substrates as small as dinucleotides. The same ribozyme is even capable of acting as a phosphotransferase and an acid phosphatase, reactions involving a terminal phosphate. [Citations omitted.]

The following discussion concerns art which is not admitted to be prior art to the claims of the present invention.

Perrotta and Been, 350 *Nature* 6317, 1991, describe the structure of HDV genomic and anti-genomic RNAs, and state that the self-cleaving element from the genomic strand RNA of HDV requires only one nucleotide 5' to the break site and either 82 nucleotides or, in the presence of denaturants, 84 nucleotides 3' to the break site for self-cleaving activity.

Rosenstein and Been, 19 *Nucleic Acids Research* 5409, 1991, propose a base-paired structure for the genomic and anti-genomic self-cleaving elements of HDV.

Branch and Robertson, 88 *Proc. Natl. Acad. Sci. USA* 10163, 1991, describe trans-cleavage by HDV modified to separate the RNA into what are believed to be the enzyme and substrate components. These two components were later combined and stated to give efficient RNA processing reactions and the correct RNA termini. They note that Perrotta and Been, *Nucleic Acids Research*, supra:

> have shown that the first five or six residues present in [Branch and Robertson's] substrate transcripts are not required for cis cleavage, a result consistent with [Branch and Robertson's] preliminary studies of antigenomic transcripts containing only three bases on the 5' site of the cleavage site. Further kinetic studies will be needed to determine how the efficiency of trans cleavage is affected by potential base pairing between the 5' end of the substrate and the 3' end of the enzyme. The potential for such base-pairing interaction was enhanced in [Branch and Robertson's] trans reactions by the addition of residues not present in δ RNA to the 3' end of the enzyme transcripts.

SUMMARY OF THE INVENTION

This invention concerns the construction and use of substrate RNA-cleaving enzymatic RNA molecules, for example, those derived from hepatitis delta virus (HDV), which need only base pair with a substrate RNA molecule 3' from the cleavage site in the substrate RNA molecule to exhibit their RNA cleaving activity on the substrate RNA. The invention also provides the first enzymatic RNA molecules which need bind only 3' or 5' of a cleavage site in a substrate RNA to cleave that site by use of an adjacent 2' hydroxyl group. This contrasts with enzymatic RNA molecules derived from Tetrahymena which bind 5' from the cleavage site on the substrate RNA and require a guanosine compound for cleavage. It also contrasts with so-called hairpin and hammerhead ribozymes which bind both 3' and 5' to a cleavage site on substrate RNA and use an adjacent 2' hydroxyl to cause cleavage.

Thus, applicant provides for the first time a means by which cleavage of separate (substrate) RNA molecules can be achieved by enzymatic RNA molecules which bind only 3' from a cleavage site. These enzymatic RNA molecules need only base pair with as few as 7 substrate nucleotides in order to exhibit the desired activity, compared to the 12–15 nucleotides generally required for hammerhead and hairpin enzymatic RNA molecules. This is slightly longer than the 4–6 nucleotide target for the Tetrahymena intron-derived enzymatic RNA molecules. Thus, these enzymatic RNA molecules are advantageous over previously described enzymatic RNA molecules since they can be provided as relatively short RNA molecules and yet specifically target relatively short target sequences. They are advantageous over those which recognize only 4–6 nucleotides since they still allow a high degree of specificity of action at any particular RNA target with little or no action at any other target.

The enzymatic RNA molecules of this invention can be designed to cleave at almost any 7 or 8 nucleotide site, having only a preference for a guanosine base immediately 3' to the cleavage site, a preference for U, C or A immediately 5' to the cleavage site, and the availability of a 2' hydroxyl group for cleavage to occur. Thus, these enzymatic RNA molecules provide significant in vitro and in vivo activities which can be used for diagnostic and therapeutic procedures.

For clarity, enzymatic RNA molecules of this invention are termed enzymes rather than ribozymes to indicate their intermolecular cleaving enzymatic nature. That is, these molecules act to cleave other RNA molecules, separate from themselves.

Thus, in a first aspect, the invention features a nucleic acid molecule having an RNA substrate cleaving enzymatic activity which cleaves a separate RNA substrate at a cleavage site. The nucleic acid molecule includes an RNA substrate binding portion which base pairs with the RNA substrate only 3' of the cleavage site, and an enzymatic portion (which may include a part or all of the RNA substrate binding portion) having the enzymatic activity. The nucleic acid molecule is able to base pair with the RNA substrate only 3' of the cleavage site, and cause cleavage of the RNA substrate at that cleavage site.

In a related aspect, the invention features a method for cleaving an RNA substrate at a cleavage site by causing base pairing of the RNA substrate with a nucleic acid molecule only 3' of the cleavage site. Such a method includes contacting the RNA substrate with a nucleic acid molecule having an RNA substrate cleaving enzymatic activity which cleaves a separate RNA substrate at a cleavage site. This nucleic acid molecule includes an RNA substrate binding portion, which base pairs with the RNA substrate only 3' of the cleavage site, and an enzymatic portion (which may include a part or all of the RNA substrate binding portion) having the enzymatic activity. The nucleic acid molecule is able to base pair with the RNA substrate only 3' of the cleavage site, and causes cleavage of the RNA substrate at the cleavage site. The contacting is performed under conditions in which the nucleic acid molecule causes cleavage of the RNA substrate at the cleavage site.

In another related aspect, the invention features a nucleic acid molecule having an RNA substrate cleaving enzymatic activity which cleaves a separate RNA substrate at a cleavage site. The molecule includes an RNA substrate binding portion which base pairs with the RNA substrate only 3' or 5' of the cleavage site, and not both 3' and 5' of the cleavage site, and an enzymatic portion (which may include a part or all of the RNA substrate binding portion) having the enzymatic activity. The nucleic acid molecule is able to base pair with the RNA substrate only 3' or 5' of the cleavage site, and causes cleavage of the RNA substrate at the cleavage site by an adjacent 2' hydroxyl group. This 2' hydroxyl group is generally provided by the substrate RNA molecule.

In preferred embodiments of the above aspects, the nucleic acid molecule is derived from hepatitis delta virus; the nucleic acid molecule is active to cleave 5' to the RNA substrate sequence of GNNNNNN, or NNNNNNN, where each N independently can be any specified nucleotide base; the nucleic acid molecule includes at least one ribonucleotide which base pairs adjacent the cleavage site; the nucleic acid molecule is RNA; the nucleic acid is a mixture of RNA and DNA; the nucleic acid molecule base pairs with a target RNA sequence consisting of or consisting essentially of 7 nucleotides; the nucleic acid molecule is circular; and the nucleic acid molecule is active to cut an RNA duplex having a single GU base pair followed by six Watson-Crick base pairs (e.g., those chosen from AU, GC, and AT).

In another aspect, the invention features a nucleic acid molecule having an RNA substrate cleaving enzymatic activity which cleaves a duplex RNA substrate at a cleavage site. The nucleic acid molecule includes an enzymatic portion able to recognize the RNA duplex and cleave the RNA duplex 5' of the G in a GU base pair, e.g., an RNA duplex having the structure:

GNNNNNN
UNNNNNN.

Alternatively, the nucleic acid molecule is active to cleave an RNA (i.e., a structure connected by Watson-Crick base pairs) duplex in a guanosine-independent manner.

In a related aspect, the invention features a method for cleaving an RNA duplex in a guanosine-independent manner, or an RNA duplex having the structure

GNNNNNN
UNNNNNN.

The method includes the step of contacting the RNA duplex with a nucleic acid molecule having an RNA substrate cleaving enzymatic activity which cleaves the duplex RNA substrate at a cleavage site. This nucleic acid molecule includes an enzymatic portion having the enzymatic activity, e.g., one able to cleave the substrate 5' of the G in the GU base pair.

In yet another aspect, the invention features a circular nucleic acid molecule, and method of making such a molecule, having an enzymatic activity which cleaves a separate RNA substrate at a cleavage site. In general, a self-ligating and self-cleaving RNA molecule containing the RNA to be circularized is incubated under suitable conditions to cause the RNA to be circularized as described below. Such a self-ligating self-cleaving RNA may be a group I or II intron or derived from a pre-mRNA intron which is not self-cleaving but will ligate in vivo with cellular factors.

Other features and advantages of the invention will be apparent from the following description of the preferred embodiments thereof, and from the claims.

DESCRIPTION OF THE PREFERRED EMBODIMENTS

The drawings will first briefly be described.

Figure 1A:
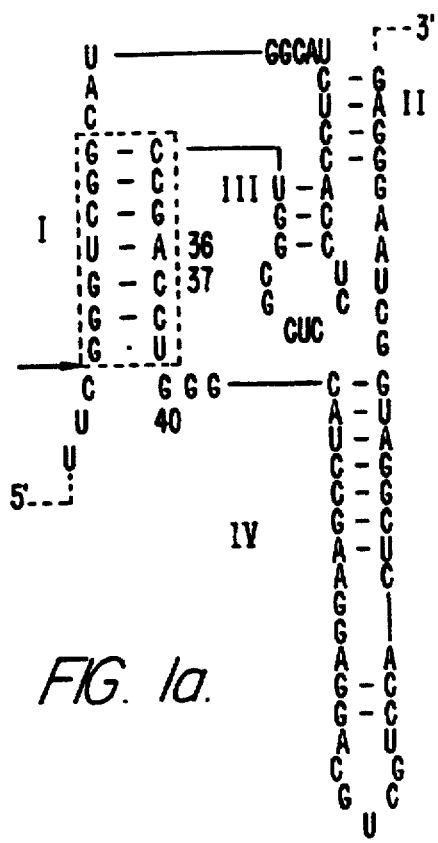

Drawings FIG. 1A (SEQ ID No.6) is a diagrammatic representation of the nucleotide base sequence and potential secondary structure of the self-cleaving sequence, SA1-2, drawn as proposed by Perrotta & Been, supra 1991 and Rosenstein & Been, 29 *Biochemistry* 8011, 1991. The site of cleavage is shown by an arrow.

Figure 1B:
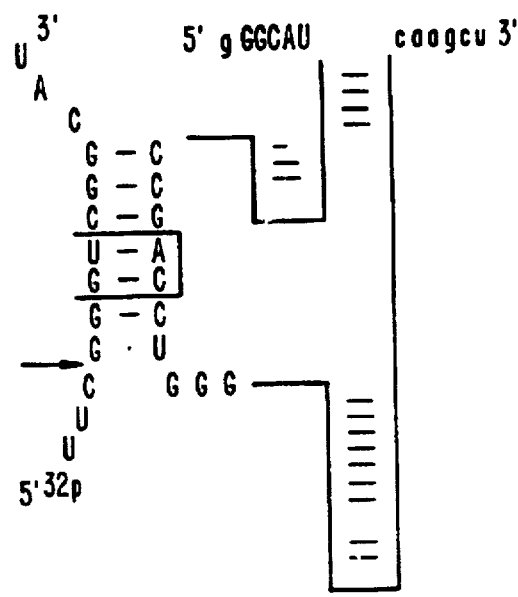
Figure 1C:
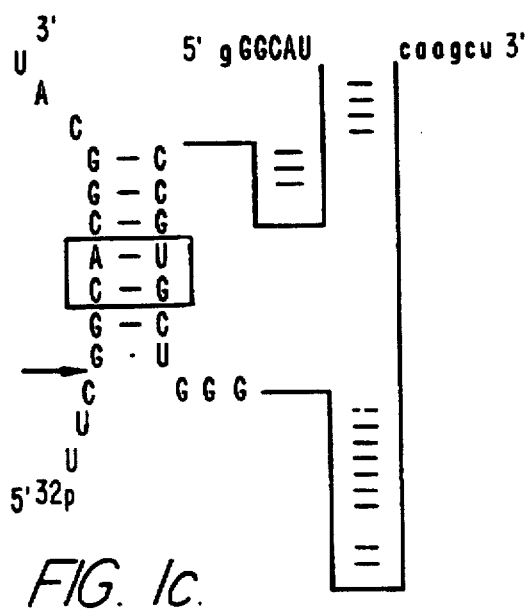

FIGS. 1B (SEQ ID No.8) and 1C (SEQ ID No.10) are diagrammatic representations of the nucleotide base sequences and potential secondary structures of RNA molecules ADC1 (FIG. 1B) and ADC2 (FIG. 1C) drawn base-paired with the substrates, DHS1 (SEQ ID No.7) and DHS3 (SEQ ID No.9), respectively. The boxed region in FIGS. 1B and 1C mark the regions where the sequences vary. In FIGS. 1B and 1C, nucleotide sequences identical to those in FIG. 1A are shown in bold lines (with base pairs indicated by horizontal lines), lower case letters are used to show sequences present in the transcripts that were contributed by the promoter or vector, and are not considered to be part of the enzymatic portion of the RNA molecule.

Figure 1E:
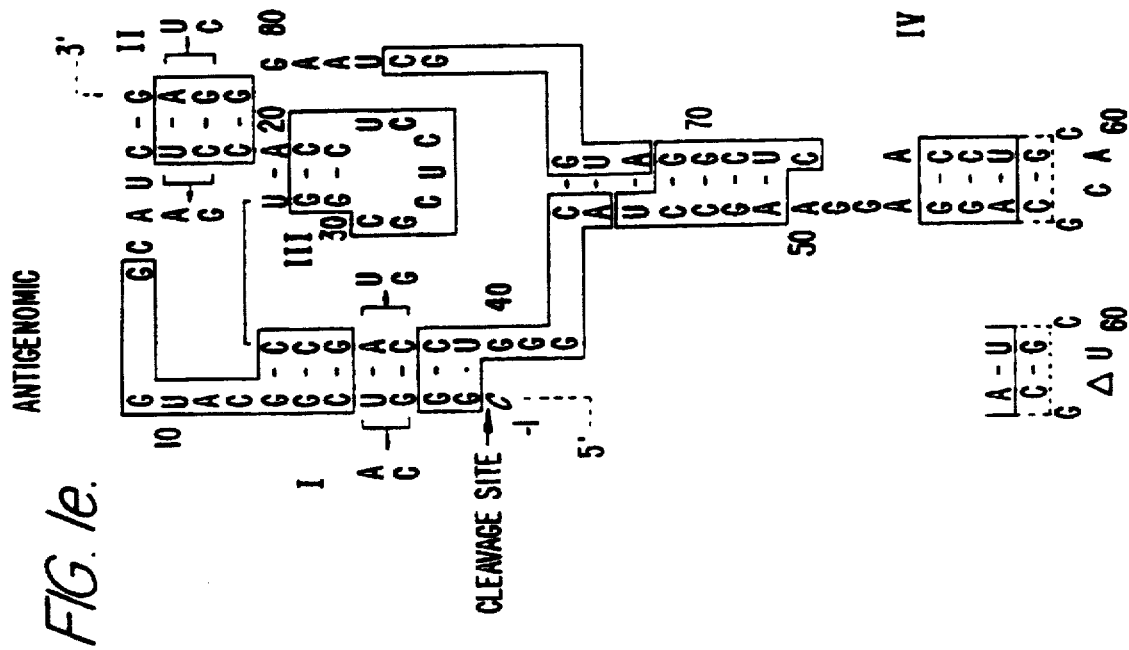
Figure 1D:
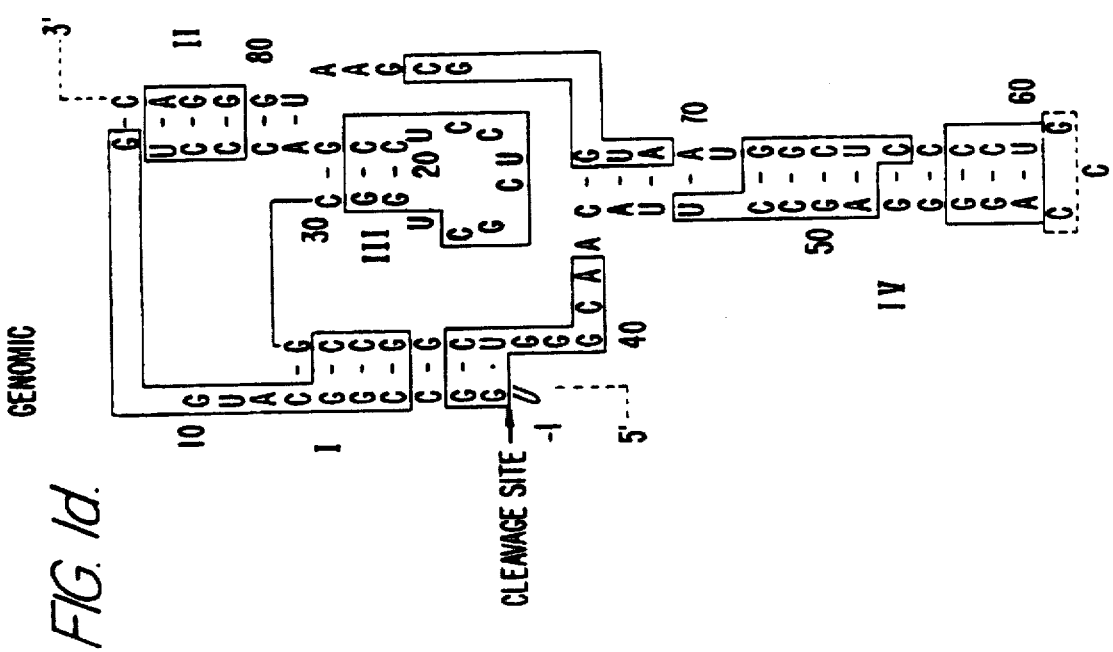

FIGS. 1D (SEQ ID No.11) and 1E (SEQ ID No.12) are similar diagrammatic representations of genomic and antigenomic RNA of HDV showing variations in sequence from FIG. 1A.

Figure 1F:
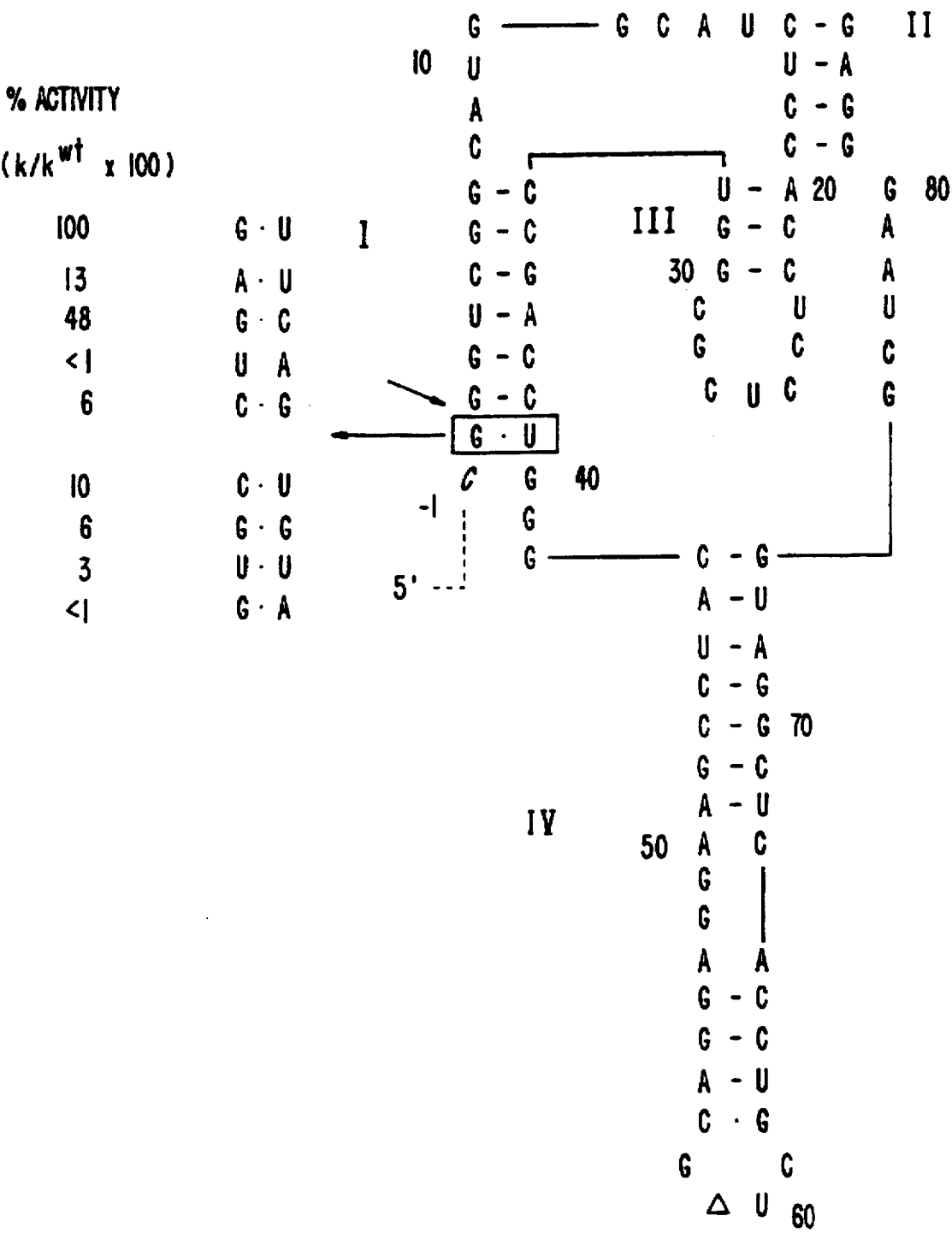
Figure 1G:
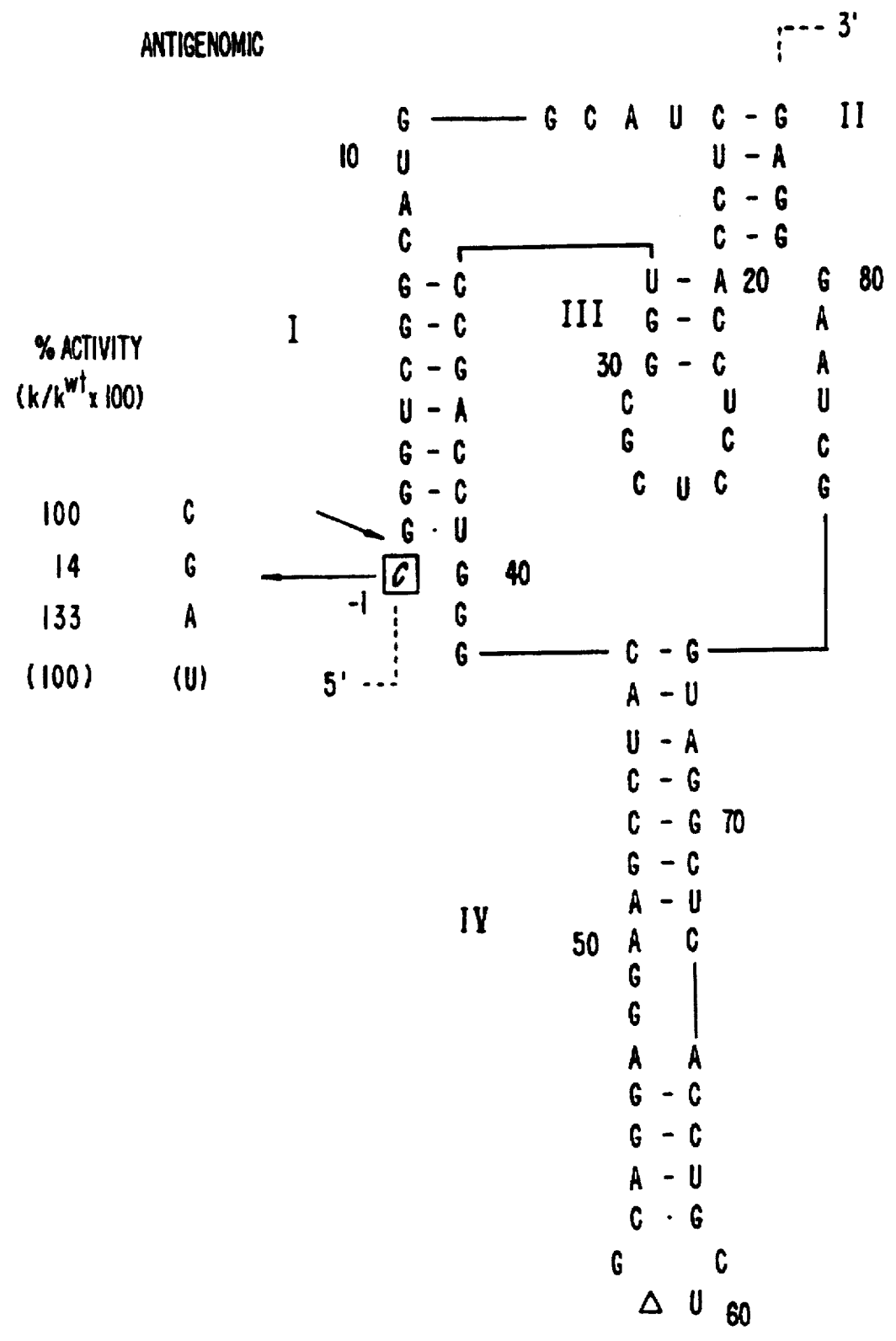
Figure 1H:
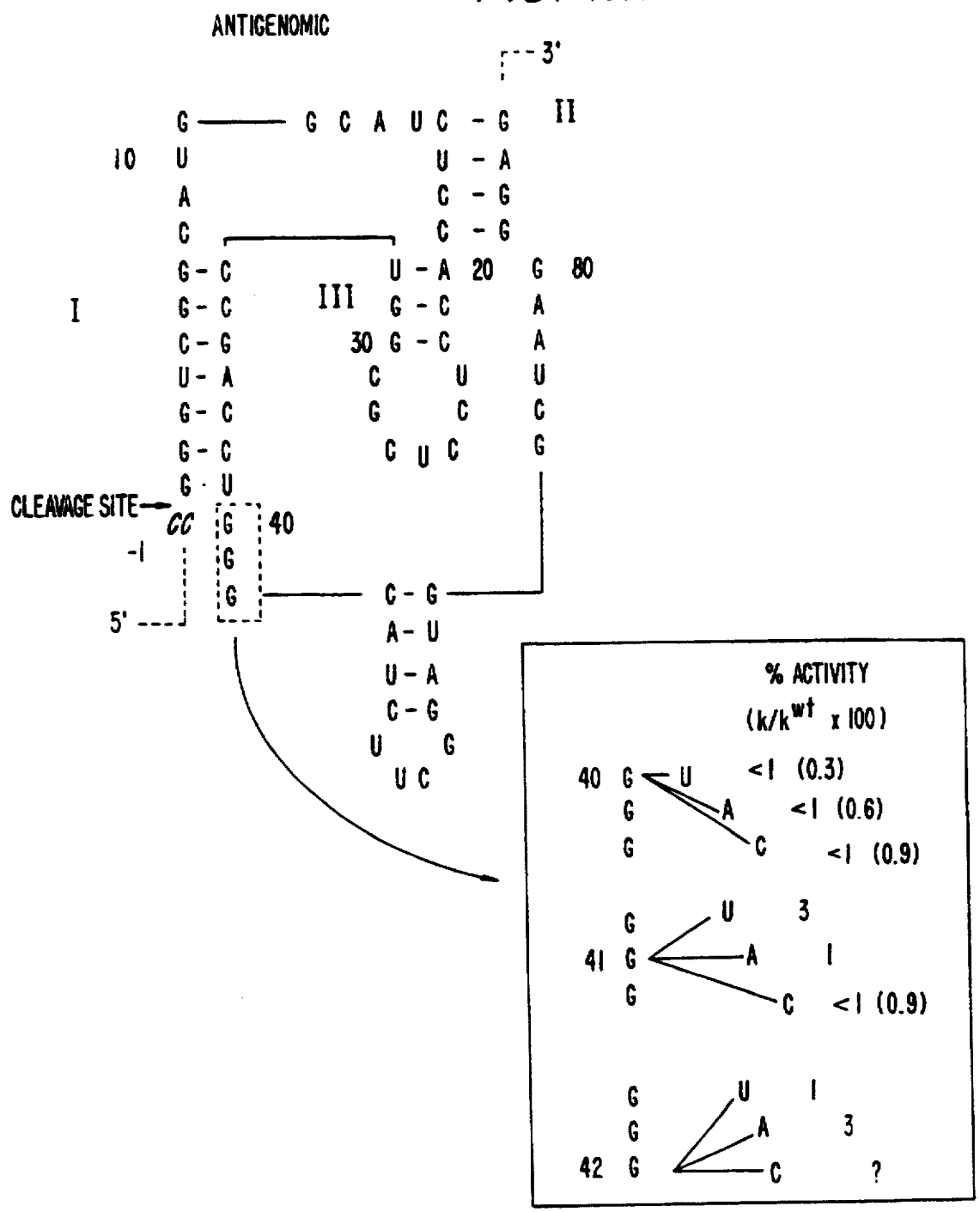

FIGS. 1F–1H (SEQ ID Nos.13–15) are diagrammatic representations of examples of modified RNA enzymes showing relative activity.

Figure 2:
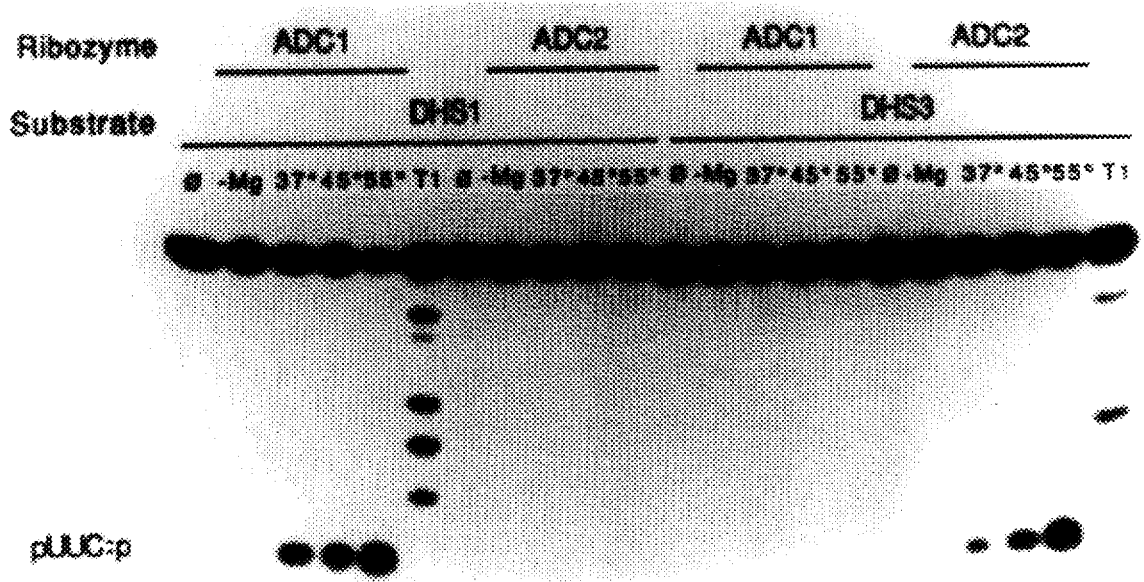

FIG. 2 is a reproduction of an autoradiogram showing trans cleavage of "matched" substrate. Substrate oligonucleotides, DHS1 and DHS3 (radioactively 5'-end labeled), were incubated with either ADC1 or ADC2 at 37° C., 45° C., or 55° C., as indicated. The reactions, containing 40 mM Tris HCl (pH 8.0 at 25° C.), 1 mM EDTA, 11 mM $MgCl_2$, and 1.5 μM substrate, were initiated by addition of enzymatic RNA to 0.3 μM and then incubated at the indicated temperatures. The pH of the complete reaction varied from 7.7 at 37° C. to 7.4 at 55° C. Reactions were terminated after 30 min by addition of 10 μl formamide containing 25 mM EDTA, and fractionated by electrophoresis on a 20% polyacrylamide gel. Control reactions were incubated for 30 min at 55° C. in the absence of either the enzyme (∅) or MgCl$_2$ (−Mg). Marker lanes (T1) contained T1-partial digests of the substrate oligonucleotide. The position of the end-labeled cleavage product (pUUC>p) is indicated.

Figure 3A:
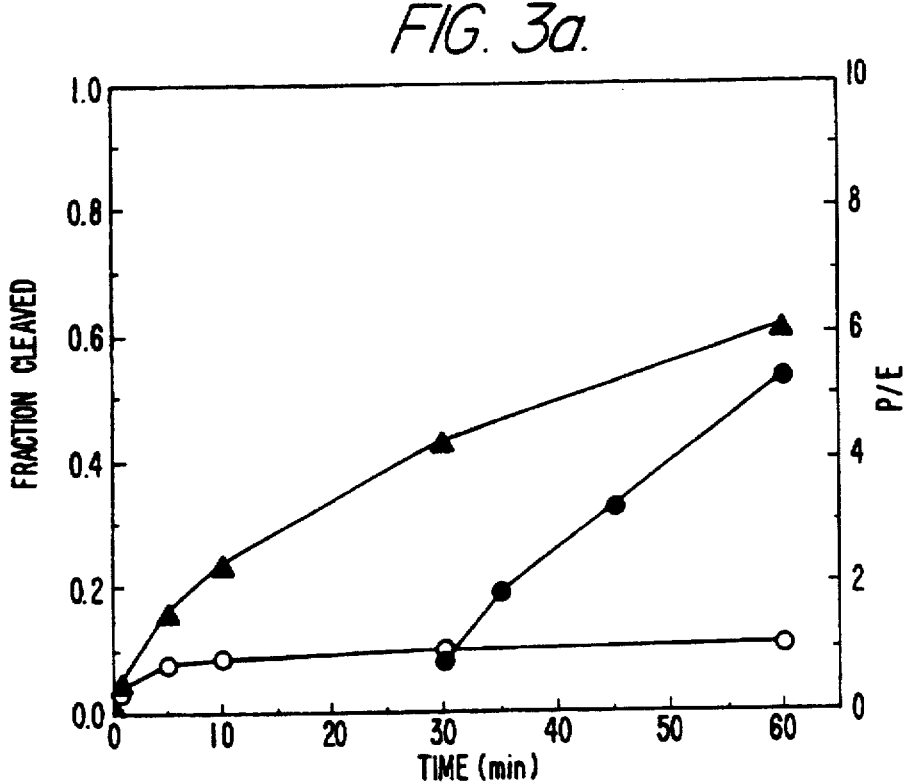
Figure 3B:
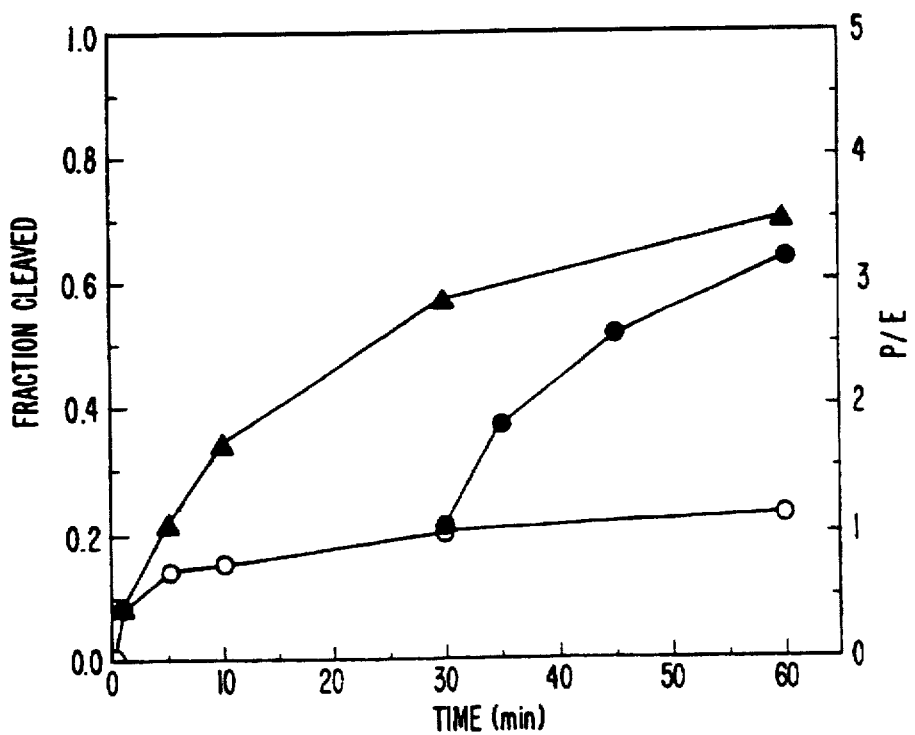

FIGS. 3A and 3B are graphical representations showing enzymatic RNA turnover at 55° C. In FIG. 3A substrate RNA ([5'-$^{32}$P] DHS1) and enzymatic RNA (ADC1) were preincubated separately for 3 min at the reaction temperature in 40 mM Tris HCl, 1 mM EDTA, 11 mM MgCl$_2$ (pH 7.7 at 37° C., pH 7.4 at 55° C.) and then mixed to start the reaction. After mixing, the concentration of DHS1 was 2 μM and the concentration of ADC1 was 0.2 μM. Samples (5 μl) were removed at the indicated times and quenched with an equal volume of formamide containing 25 mM EDTA, and fractionated by electrophoresis on a 20% polyacrylamide gel. Labeled substrate and product bands were quantified and the results expressed both as the fraction of the total radioactivity in each lane present in the product, and as the moles of product generated per mole of enzymatic RNA (P/E). At 55° C., 90–92% of the substrate was cleaved; the data have not been corrected for this end-point. Filled triangles, reaction at 55° C. Open circles, reaction at 37° C. Filled circles, reaction incubated at 37° C. and then shifted to 55° C. after 30 min. In FIG. 3B, the experiment was done as in FIG. 3A, except the enzymatic RNA concentration was increased to 0.3 μM, and the substrate concentration reduced to 1.5 μM.

Figure 4A:
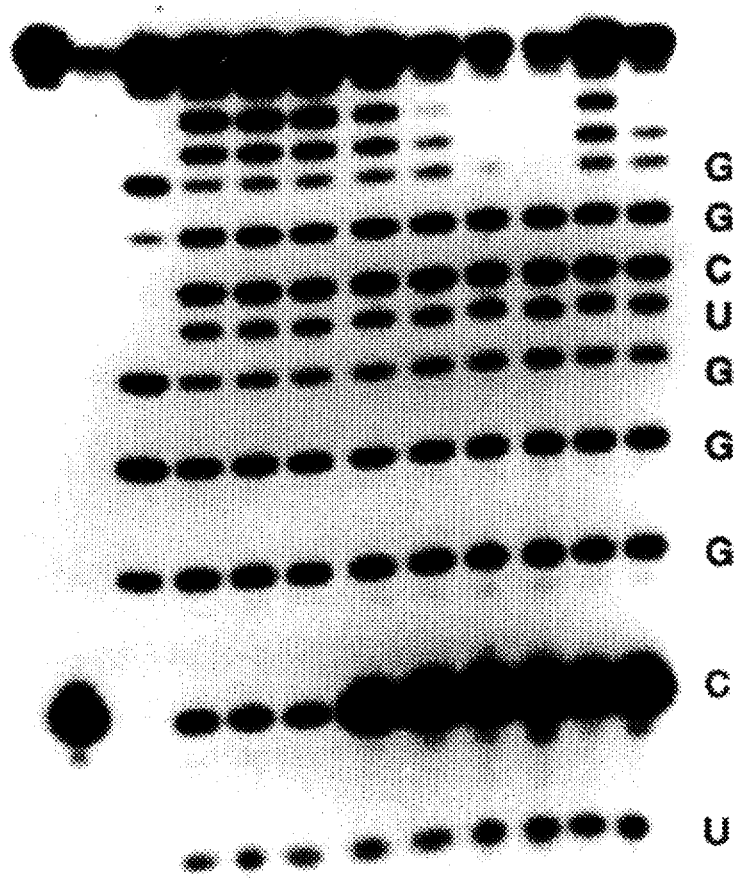
Figure 4B:
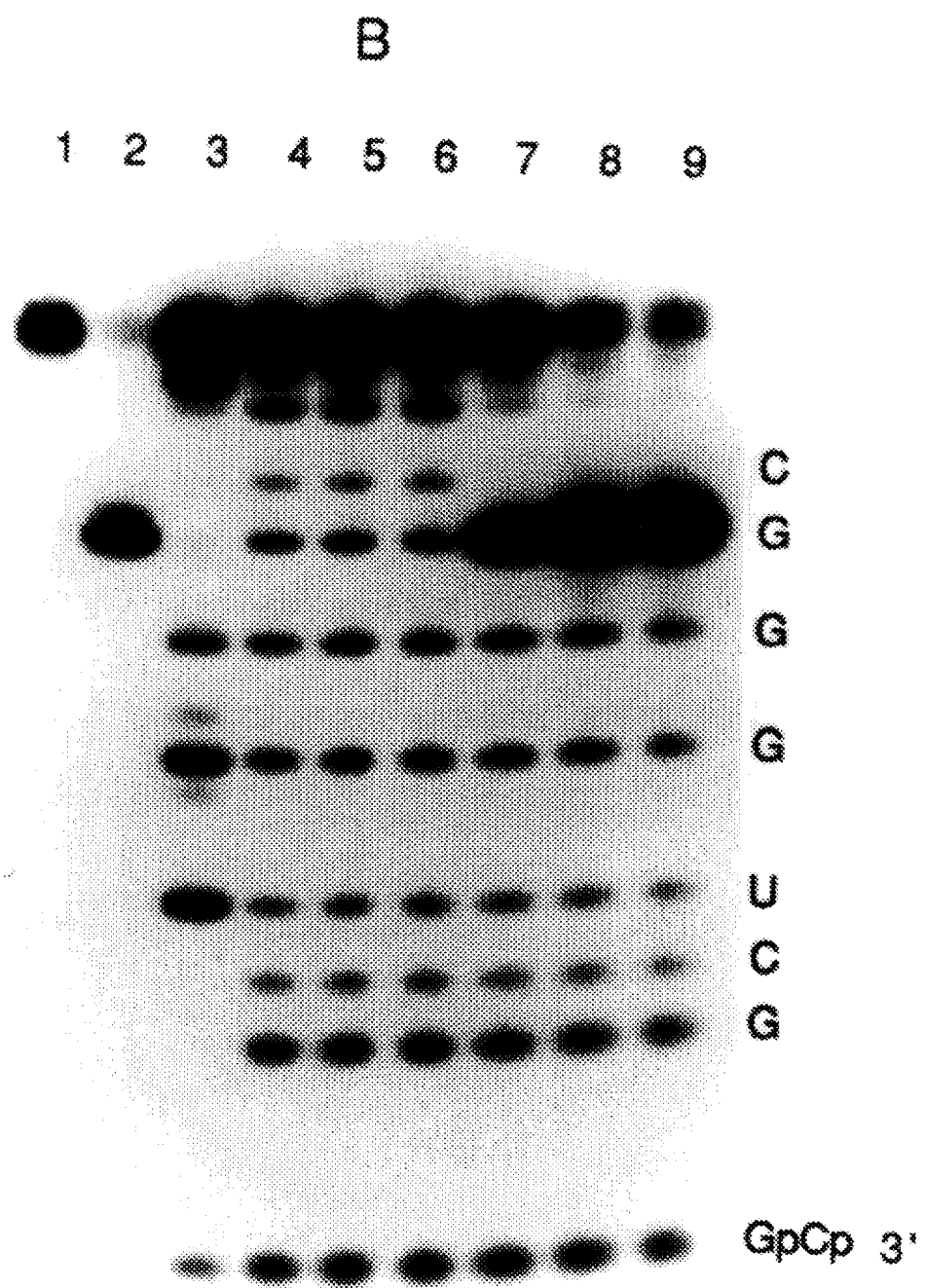

FIGS. 4A and 4B are reproductions of autoradiograms allowing estimation of the substrate target size. Specifically, FIG. 4A demonstrates the requirements 3' to the site of cleavage. An alkaline hydrolysis-generated partial digest of 5' end-labeled substrate oligonucleotide, DHS1 (lane 4), was incubated with 0.3 μM ADC1 at 50° C. in 0 mM (lane 6), 2 mM (lanes 7 and 8), or 10 mM Mg$^{2+}$ (lanes 9–12) for 5 min (lanes 7, 9, and 11) or 30 min (lanes 8, 10, and 12). In addition to the Mg$^{2+}$, which was used to initiate the cleavage, reactions shown in lanes 5–12 contained 30 mM Tris/HCl, 7 mM sodium bicarbonate (pH 7.5), and 0.5 mM EDTA; reactions shown in lanes 11 and 12 also contained 2M urea. The amount of total substrate in each reaction was estimated to be less than 25 nM. Samples were prepared for electrophoresis by mixing 5 μl of the reaction with an equal volume of formamide containing 25 mM EDTA. Products were fractionated on a 20% polyacrylamide/7M urea gel. Markers and controls: lane 1, labeled DHS1 untreated; lane 2, DHS1 cut by ADC1 in 10 mM Mg$^{2+}$ for 10 min at 50° C.; lane 3, T1 partial digest of DHS1; lane 5, the alkaline digest incubated at 50° C. for 30 min in 10 mM Mg$^{2+}$ without enzymatic RNA.

FIG. 4B demonstrates the requirements 5' to the site of cleavage. An alkaline generated partial digest of 3' end-labeled DHS2 (UUC^GGGUCGGp*CP) (SEQ ID No.1) (lane 4) was incubated at 50° C. with 0.3 μM ADC1 in 0 (lane 6), 2 (lane 7), 10 (lane 8), or 20 mM Mg$^{2+}$ (lane 9). The reactions were terminated after 5 min by the addition of an equal volume of formamide containing 25 mM EDTA. Reaction conditions were otherwise as described in FIG. 4A (markers and control lanes 1–3 and 5 were equivalent of those described above). The conditions used for 3' labeling and partial digestion by alkali or T1 are described in Perrotta & Been, supra, 1990 and 1991.

Figure 5A:
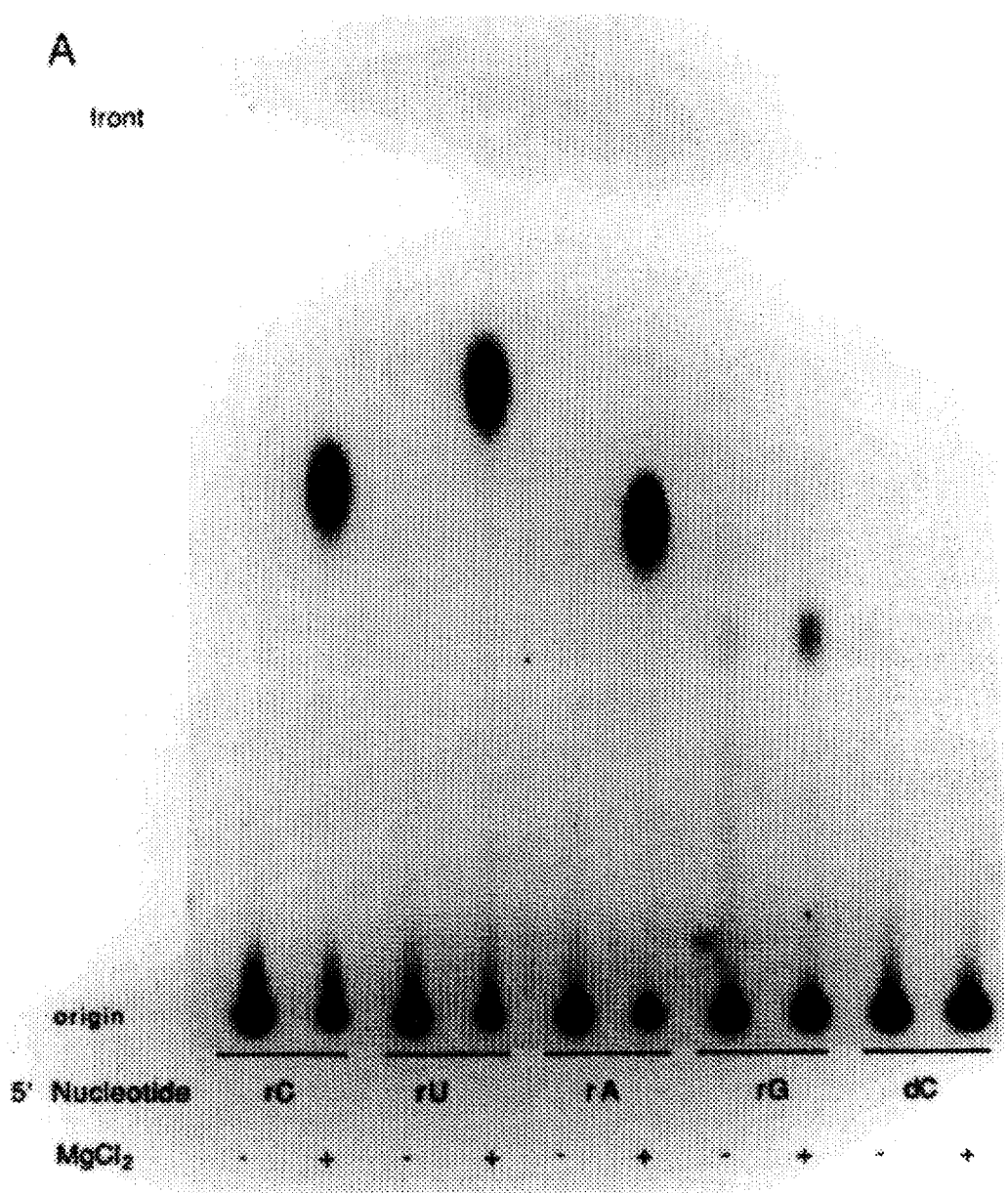

FIG. 5A is a reproduction of an autoradiogram of a PEI thin layer chromatography plate showing the effect of changes in the nucleotide present in substrate RNA at the position 5' to the cleavage site. Specifically, trace amounts of oligonucleotides of the sequences [5'$^{32}$P]pN^GGGUCGG (where N is the nucleotide indicated in the figure) were incubated in 10 μl reactions at 55° C. in 40 mM Tris-HCl (pH 7.4), 1 mM EDTA, 1 μM ADC1, with and without 11 mM MgCl$_2$ as indicated. The enzymatic RNA was added last. After 5 minutes, 2.5 μl of 0.1M EDTA was added to stop the reaction, and 2 μl from each reaction fractionated on a PEI plate. The position of adenosine 2',3' cyclic phosphate 5' phosphate marker is indicated by the dashed oval.

Figure 5B:
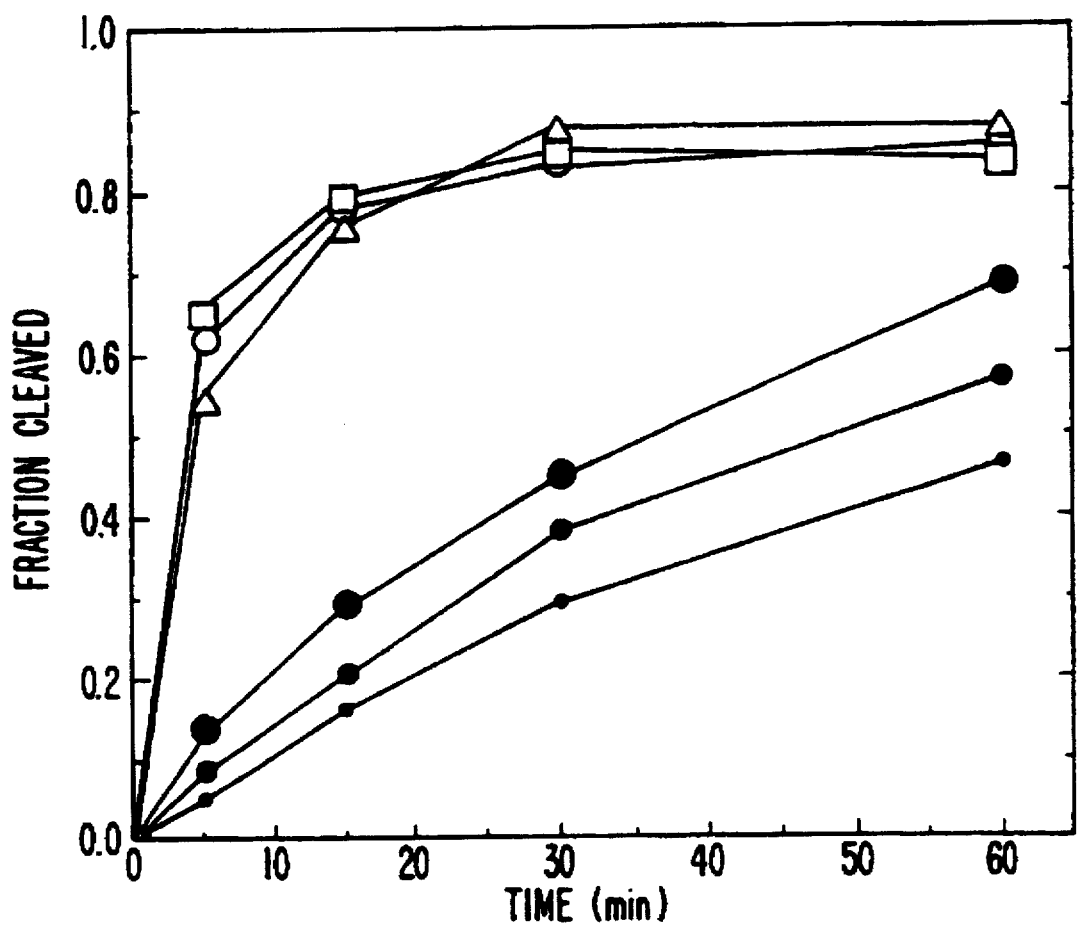
Figure 6:
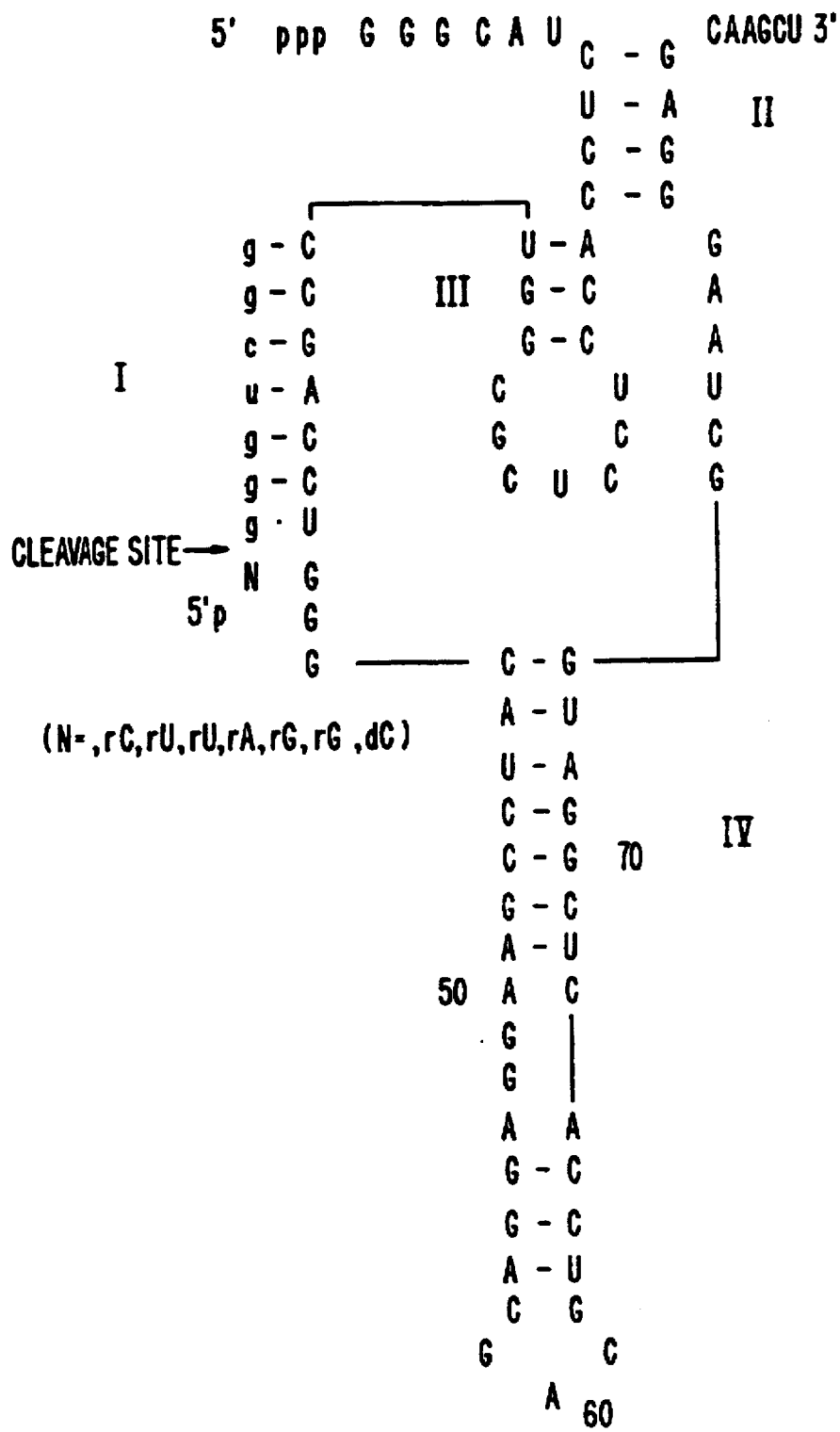
Figure 8:
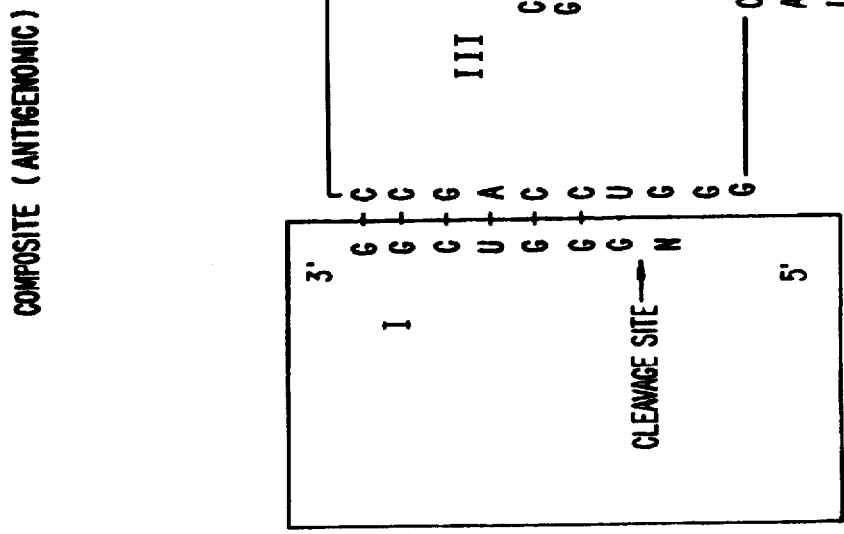

FIG. 5B is a graphical representation of cleavage of substrate RNA over time. Reactions were as described in FIG. 5A except the concentration of ADC1 was varied in the reaction with DHS8 (5'G). The PEI plate was prespotted with 2.5 μl of 0.1M EDTA at the origins and, at the indicated times, 2 μl of the reaction was removed and spotted directly onto the PEI plate to stop the reaction. Open circles, DHS4 (5'C) with 1 μM ADC1; open squares, DHS5 (5'U) with 1 μM ADC1; open triangles, DHS6 (5'A) with 1 μM ADC1. Closed circles of increasing sizes, DHS7 (5'G) with 1, 2, or 4 μM ADC1. Values were not adjusted for the final extent of the reaction.

FIGS. 6–10 are diagrammatic representations of the following enzymatic RNA molecules (ADC1, ADC3, CDC200, PDC7) (SEQ ID Nos.16–21) and related substrates, and a duplex cleaving enzyme, respectively.

FIG. 11 is a diagrammatic representation showing RNA molecules adapted for formation of a circular (C) enzymatic RNA molecule. A wild-type intron secondary structure is shown schematically in the upper left, and secondary structures of the permuted intron sequences shown in the remainder of the figure. The heavy line represents the exon sequence(s), the light line represents the intron sequence, and the dotted dark line represents vector sequences added to the permuted forms. The arrow points to the 5' splice site. Numbers refer to specific pairings in the intron.

Figure 12A:
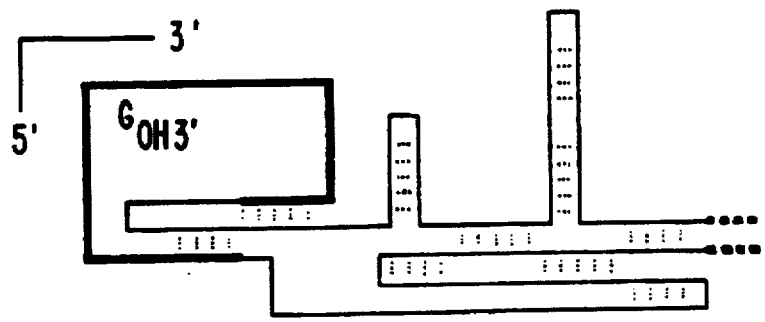
Figure 12B:
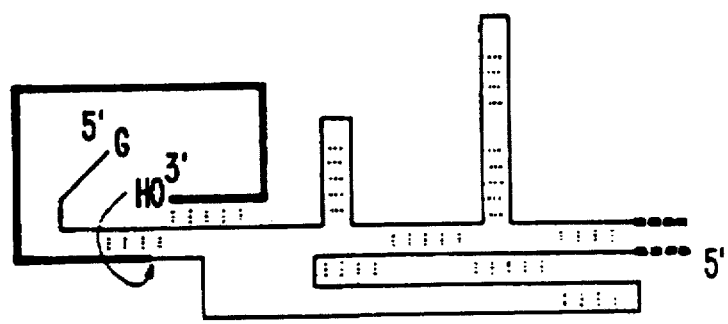
Figure 12C:
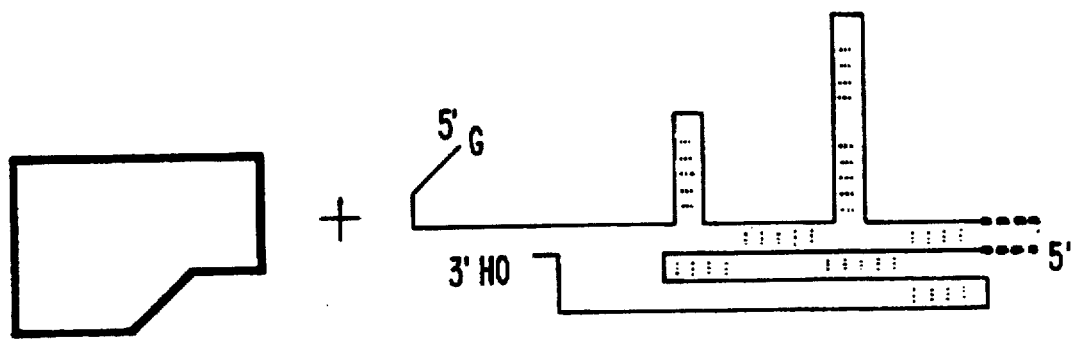

FIG. 12 shows diagrammatically the steps in formation of one example of a circular RNA molecule. Initially, guanosine attacks at the 5' splice site of the permuted RNA containing the RNA sequence to be circularized (dark line). Attack then occurs by the new 3' hydroxyl group of the 3' splice site, resulting in the covalent closure of the "internal exon" sequence to form a circular RNA.

ENZYMATIC RNA MOLECULES

Enzymatic RNA molecules of this invention are generally described above. Below are provided examples of such molecules. These examples are not limiting in the invention and are provided only to specifically illustrate the invention to the reader. Those in the art will recognize that these examples and accompanying description enable practice of the claims presented below.

As discussed above, specific cleavage of substrate RNA by these molecules requires only base pairing 3' to the site of cleavage. The mechanism of cleavage of the enzymatic RNA molecules also differs from that described for the Tetrahymena-derived (e.g., L-19) RNA molecules, since attack on the cleavage site phosphorous is by an adjacent endogenous 2'-hydroxyl group rather than the 3'-hydroxyl group of an exogenous guanosine. Thus, this is the first description of enzymatic RNA which causes cleavage at a site by an adjacent 2' hydroxyl group with base-pairing required on only one side of the cleavage site. Below is provided the first demonstration, for the HDV enzyme, of enzymatic RNA in which the 2' hydroxyl is required for such specific cleavage.

Referring to FIG. 1A, the RNA sequence that is used in the examples below to demonstrate the enzymatic trans-reaction was derived from, but is not identical to, the self-cleaving sequence from the antigenomic (minus) strand of HDV. Referring to FIGS. 1D and 1E, the self-cleaving sequences from genomic and antigenomic HDV can be used in similar ways to develop enzymatic RNA molecules with similar properties. Indeed, a synthetic version which is a composite of the two sequences, CDC200 (see FIG. 8 and below), is also active. As shown in FIGS. 1F–1H, significant differences in RNA sequence can exist between various enzymatic RNAs of this invention. This fact supports the broad scope of the claims below.

As is obvious from the examples below, almost infinite changes can be made in stem I of HDV (see FIG. 1). Although changes at every position involved in stem I pairing have not been made, it appears that only the base at +1 in the substrate (the first position 3' to the cleavage site) cannot easily be altered, that is, the G at that position seems to be important for the cleavage reaction to occur at greatest efficiency. Changes in the binding site indicate that bases at +2 to +7 are recognized through Watson-Crick pairing. Therefore, it is possible to design any desired enzyme to cleave 5' to the substrate sequence, GNNNNNN, where N can be any specified nucleotide base.

Figure 7:
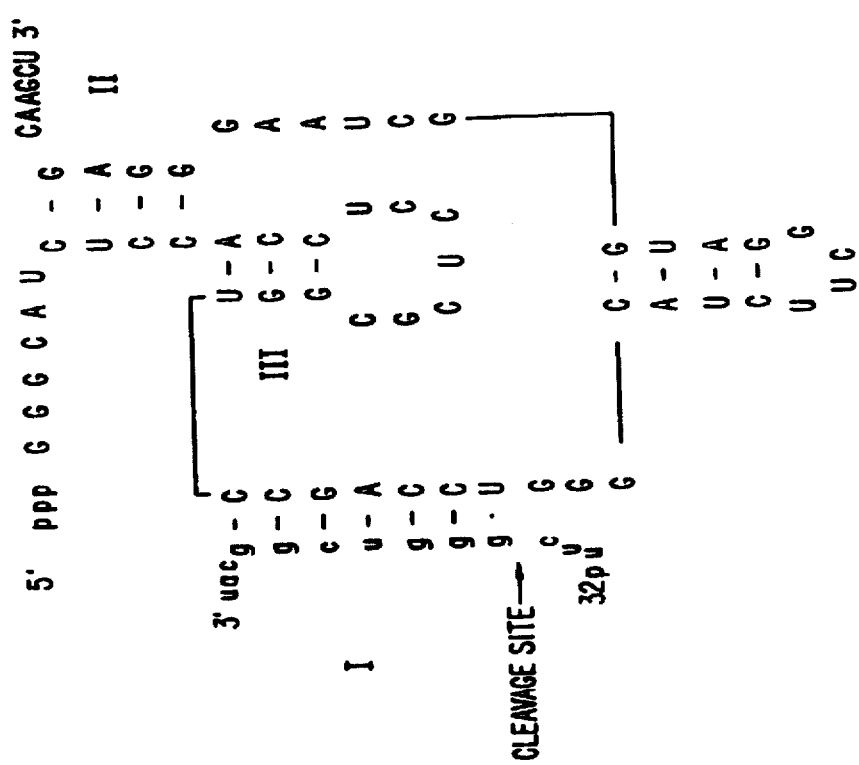

It also appears to be possible to change the size of the target sequence by extending (or shortening) stem I, this may affect activity to some extent. There are several variations on this enzyme which can be made by changing the sizes and sequences of stems II or IV. FIG. 7 shows one that was tested in which stem IV is shortened (ADC3). This smaller version appears to be at least as active as ADC1 (see FIG. 6), however in cis, self-cleavage is faster than the version with the longer stem IV; thus, the smaller enzymes could be more active. In the self-cleaving form of the RNA molecule, changes in the sequence to stem IV in ADC3, and stem II in ADC1 enhances rates of cleavage over the original versions. Many sequences can be eliminated which are not required for enzymatic activity. For example, FIG. 8 (CDC200) shows an RNA molecule which was made and shown to be active. Such smaller enzymatic RNAs have simplified synthesis and the potential for higher specific activity due to a higher probability that a small RNA will fold into an enzymatically active structure.

The target sequence may also include a series of bases which loop out during a cleavage reaction but still allow cleavage to occur. Thus, an enzymatic RNA molecule may be targeted to RNA substrates of varying structures.

Figure 9:
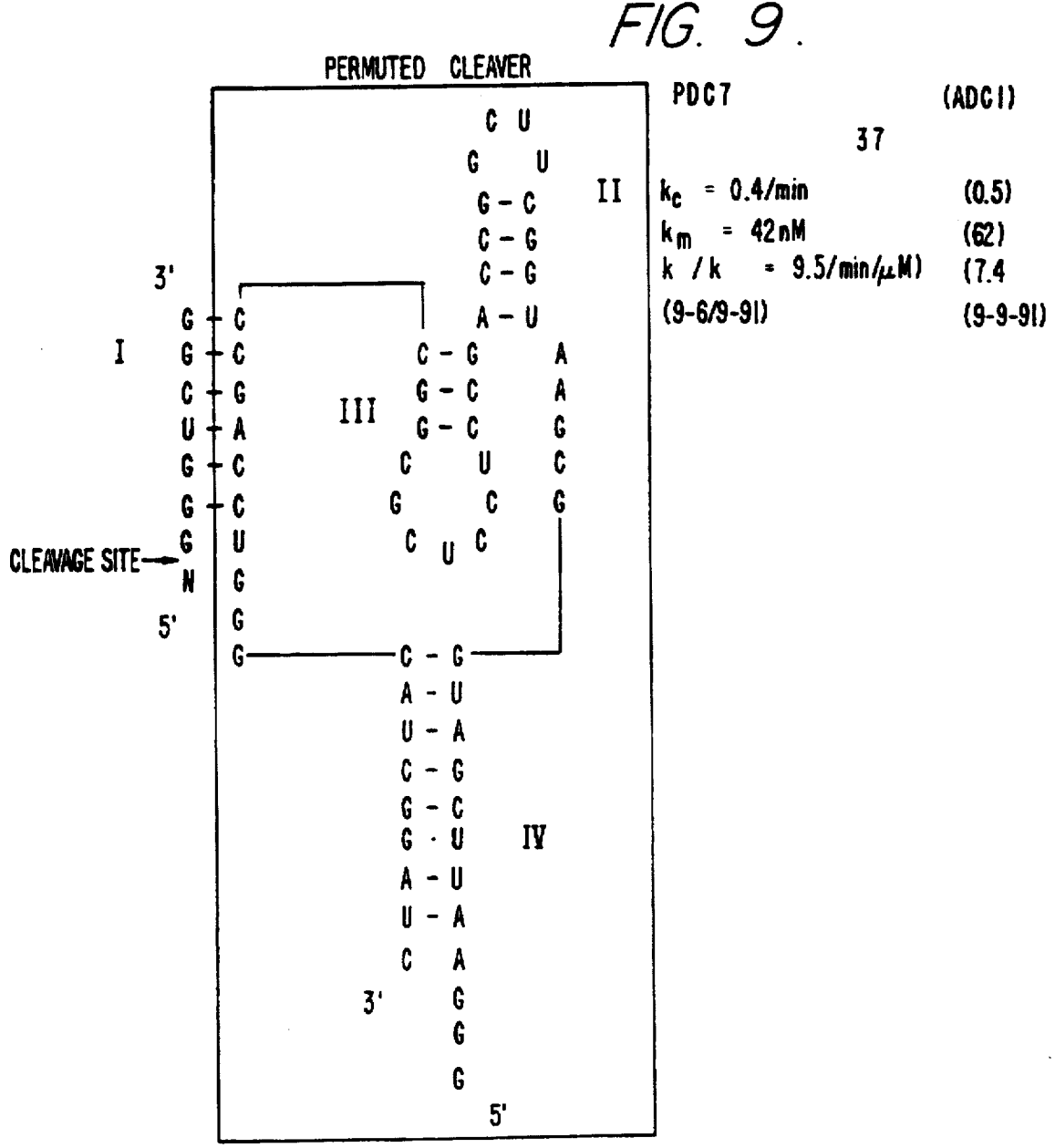

The diverse changes in RNA structure which are possible in this invention are illustrated by a version in which the open end of stem II. is closed with a loop, and stem IV is opened (FIG. 9, PDC7). This "permuted" version is also enzymatically active. From the standpoint of enzyme design, the ability to make an active enzyme may depend to a large extent on getting the RNA to fold correctly once it is synthesized. The ability to vary the position at which the polynucleotide chain starts and ends may be of some use in that regard. The fact that a circularly permuted version of the enzyme can be made suggests that it should also be possible to make a circular form of the enzyme. Such circular RNA molecules, since they would have no ends, are resistant to exonucleases which degrade RNA. Such enzymes are extremely important for therapeutic uses.

Figure 10:
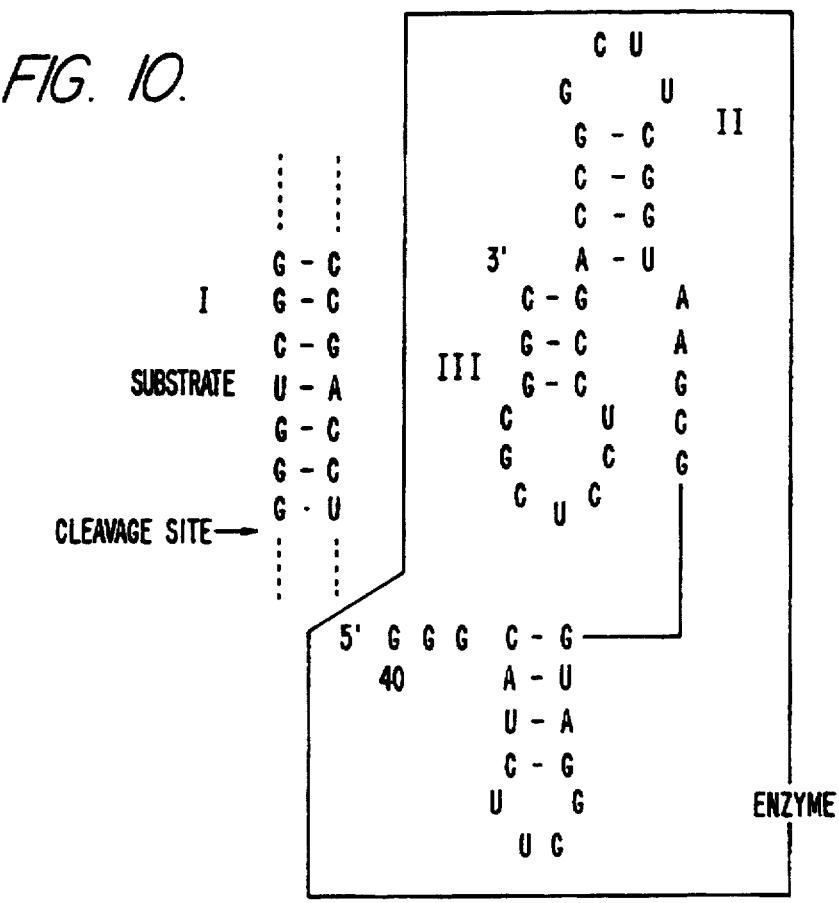
Figure 11A:
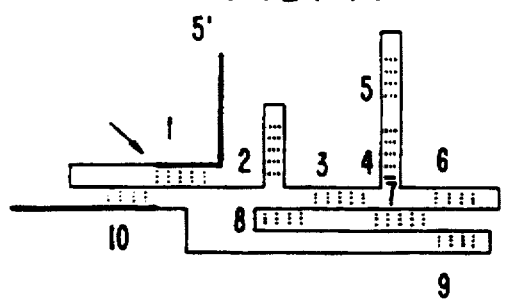
Figure 11B:
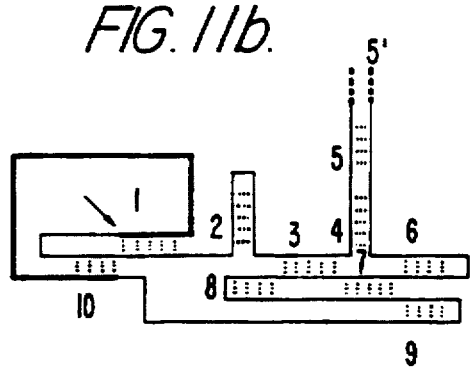
Figure 11C:
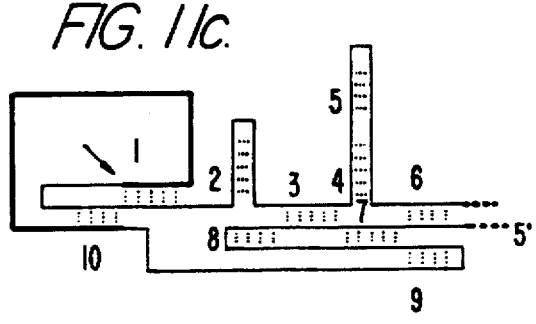
Figure 11D:
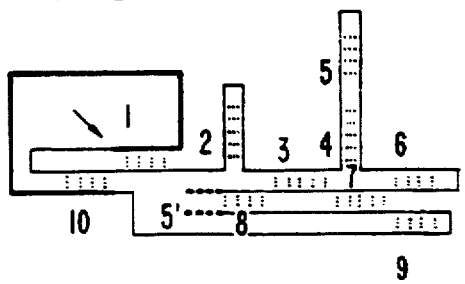

It is also possible to make a version of the RNA enzyme which, rather than cutting single-stranded RNA, cuts any RNA duplex which contains a single GU base pair followed by 6 Watson-Crick base-pairs. Referring to FIG. 10, stem I is provided as the substrate and the rest of the enzyme is provided as the remainder of the RNA sequence of HDV or its equivalent.

EXAMPLE 1

Modified HDV RNA

A self-cleaving RNA sequence from hepatitis delta virus was modified to produce an enzyme capable of catalyzing the cleavage of RNA in an intermolecular (trans) reaction. The delta-derived enzyme cleaved substrate RNA at a specific site, and the sequence specificity could be altered with mutations in the region of the enzyme proposed to base pair with the substrate. A substrate target size of approximately 8 nucleotides in length was identified. Octanucleotides containing a single ribonucleotide immediately 5' to the cleavage site were substrates for cleavage, and cleavage activity was significantly reduced only with a guanine base at that position. A deoxyribose 5' to the cleavage site blocked the reaction. These data are consistent with a proposed secondary structure for the self-cleaving form of the hepatitis delta virus enzyme in which a duplex forms with sequences 3' to the cleavage site, and they support a proposed mechanism in which cleavage involves attack on the phosphorous at the cleavage site by the adjacent 2' hydroxyl group.

Hepatitis delta virus (HDV) is a small single-stranded RNA virus that has been found in certain patients who are also infected with hepatitis B. A self-cleaving sequence present in both the genomic RNA and the complementary antigenomic RNA may act to process the RNA during rolling circle replication of the viral RNAs. The HDV RNA, therefore, is an example of an autocatalytic RNA that in its natural form functions in human cells. As with other self-cleaving RNAs, self-cleavage activity of the HDV RNA requires a divalent cation, and cleavage generates products containing a 5' hydroxyl group and a 2'.3'-cyclic phosphate.

The proposed model for the HDV self-cleaving structure shown in FIG. 1A indicates that a trans acting enzyme should bind substrate as specified by the duplex adjacent to the cleavage site (boxed region, FIG. 1A). In this example, it is shown that a catalytic form of the hepatitis delta RNA, generated by removing the 5' side of stem I, is capable of cleaving oligoribonucleotides at defined sequences. Using substrates of various sizes and sequence, evidence is provided that an intermolecular form of the stem I interaction, the cleavage-site duplex, is required for the trans reaction. The trans reaction was used to examine base and sugar requirements for the nucleotide directly 5' to the site of cleavage.

The following materials and methods were used in this example.

The plasmids pSA1-2 and pSI5'3' (Perrotta & Been, supra 1991) contained synthetic versions of the antigenomic self-cleaving element inserted downstream of a T7 promoter. pADC1 and pADC2 were generated from pSA1-2 and pSI5'3', respectively, by oligonucleotide directed deletion mutagenesis using a uracil-containing single-stranded form of the plasmids as the template (Kunkel et al., 154 *Meth. Enzym.* 367, 1987; Vieira & Messing, 153 *Meth. Enzym.* 3, 1987). The oligonucleotide (5' AGGAGGTGGAGATGCC-CTATAGTGAGTCGT) (SEQ ID No.5) was complementary to a portion of the antigenomic sequence and to a portion of the T7 promoter. It was designed to delete the region from +2 relative to the T7 promoter to +10 relative to the cleavage site in the sequence of the self-cleaving element, thus removing the 5' side of stem I in the proposed structure. Plasmids with the proper deletion were identified by sequencing miniprep DNA by primer extension with modified T7 DNA polymerase and dideoxynucleotide chain terminators. Following a second round of transformation and sequencing, plasmid DNA was prepared from overnight cultures by boiling lysis and purified by CsCl equilibrium density centrifugation in the presence of ethidium bromide.

The conditions used for transcription were: 40 mM Tris-HCl (pH 7.5), 15 mM MgCl$_2$, 5 mM dithiothreitol, 2 mM spermidine, ribonucleoside triphosphates at 1 mM each, 0.1 mg/ml linear plasmid DNA, and 50 units of T7 RNA polymerase/mg of DNA. After 60 minutes at 37° C., EDTA was added to 50 mM, formamide to 50% (v/v), and the RNA was fractionated by electrophoresis on an 8% (w/v) polyacrylamide gel containing 7M urea. RNA was located by UV shadowing, excised, eluted overnight at 4° C. (in 10 mM EDTA, 0.1% (w/v) sodium dodecyl sulfate), and recovered by ethanol precipitation. Concentrations were estimated from the base composition and extinction coefficients at 260 nm.

The substrate RNAs (DHS1, UUC^GGGUCGGCAU (SEQ ID No.2); DHS2, UUC^GGGUCGG (SEQ ID No.3); DHS3, UUC^GGCACGGCAU (SEQ ID No.4); DHS4, C^GGGUCGG; DHS5, U^GGGUCGG; DHS6; A^GGGUCGG, DHS7; G^GGGUCGG) and the mixed oligonucleotide (DHS8, dC^rGGGUCGG) were supplied by US Biochemical (Ohio), where they were chemically synthesized, deprotected, and the bases checked for deprotection by HPLC. Each was gel purified and the sequence confirmed by enzymatic sequencing of 5' $^{32}$P-labeled material. Alkaline hydrolysis of DHS8 did not release a 5' labeled mononucleotide which was consistent with the presence of a 5' deoxyribose, although the base at that position was not identified. Substrate oligonucleotides were radiolabeled in a 10 µl reaction containing 25 pmoles of oligonucleotide, 25 pmoles [gamma-$^{32}$P]ATP (7000 Ci/mmole), 50 mM Tris HCl (pH 8.9 at 24° C.), 10 mM MgCl$_2$, 5 mM dithiothreitol, and 10 units of T4 polynucleotide kinase; following incubation for 30 min at 37° C., EDTA was added and the labeled oligonucleotide was gel purified. For some experiments, trace amounts of the labeled substrates were mixed with a known amount of the unlabeled oligonucleotide. The unlabeled substrate contained a 5' OH group.

Products were fractionated by electrophoresis on 20% polyacrylamide (Bis acrylamide: acrylamide; 1:29) gels (0.7 mm thick×19 cm wide×22 cm high) containing 7M urea, 0.1M Tris-Borate pH 8.3, and 1 mM EDTA. Following electrophoresis, the gel was transferred to an acetate sheet, covered with plastic wrap and an autoradiogram prepared at −70° C. To quantify results from gels, bands were located using the autoradiogram, excised, and quantified by measuring Cerenkov scintillation.

Polyethyleneimine (PEI) plates from EM Science (sold by VWR), were prewashed with H$_2$O and dried immediately before using. Samples (2 µl) were spotted 2 cm from the bottom edge of the plate. The solvent was 1M LiCl. Quantitation was done using a Bioscan single-wire detector.

The following results were obtained:

Using a plasmid containing a cloned synthetic version of the antigenomic self-cleaving sequence (pSA1-2), the portion of the sequence forming the 5' end of the element was deleted, generating pADC1. In vitro synthesis with T7 RNA polymerase generated a HindIII runoff RNA lacking the 5' side of stem I (nucleotides 5' to position 10 were replaced by a single G in this transcript) (see FIG. 1B). A second version of the truncated sequence, pADC2, incorporated a mutation in the 3' side of stem I (A36U, C37G; see FIG. 1C).

RNAs transcribed from pADC1 and pADC2 (ADC1 and ADC2) were purified and tested for cleavage activity with two oligoribonucleotide substrates. Substrate DHS1 was a 13-mer, it contained the wild-type sequence from nt position −3 to +10 relative to the cleavage site and had the potential to form the postulated cleavage-site duplex with ADC1 RNA (FIG. 1B). DHS1 contained two mismatches in a similar interaction with ADC2. The substrate DHS3, relative to DHS1, contained two base changes, a G to C at position 3 and a U to A at position 4 so that it contains two mismatches with ADC1 but could form a cleavage-site duplex with ADC2 (FIG. 1C).

Each substrate was 5' end-labeled with $^{32}$P and incubated with either ADC1 or ADC2. Cleavage of either substrate at the correct site released a 5' end-labeled trinucleotide. [$^{32}$P] UUC. In 10 mM Mg$^{2+}$ at 37° C., 45° C., and 55° C., DHS1 was cleaved by ADC1 but not by ADC2, while DHS3 was cleaved by ADC2 but not by ADC1 (see FIG. 2). Thus, under these conditions, each form of the enzyme cleaved only the "matched" substrate with which it could form Watson-Crick base-pairs. The accuracy of the cleavage reaction was confirmed by analyzing the cleavage products on a sequencing gel adjacent to T1 and alkaline hydrolysis ladders of the end-labeled substrates. With an internally labeled substrate, made by transcription from synthetic templates, both 5' and 3' products were observed.

With a 10 fold excess of substrate (DHS1) to enzyme (ADC1), approximately 60% of the substrate was cleaved in 60 min at 55° C. (see FIG. 3A, solid triangles) indicating that 6 moles of substrate were cleaved per mole of enzyme. However at 37° C., the portion of substrate that was cleaved plateaued at about 10% (open circles). The extent of the reaction at 37° C. could represent a single cleavage event per molecule of ADC1. Consistent with that interpretation, increasing the ratio of ADC1 to DHS1 at 37° C. resulted in a larger fraction of the substrate being cleaved, but it still plateaued at approximately 1 mole of product per mole of enzyme (see FIG. 3B, open circles). If, following a 30 min incubation at 37° C., the reaction was shifted to 55° C., cleavage activity resumed (see FIGS. 3A & 3B, closed circles), indicating that the enzyme had not been inactivated during the incubation at 37° C. Addition of free enzyme after 30 min at 37° C. resulted in additional cleavage, indicating that the substrate was still in an available form. Preincubation of the enzyme at 55° C., or denaturation of the enzyme by heat prior to addition of Mg$^{2+}$ did not result in increased activity at 37° C.

Preferred substrate target size is consistent with the proposed cleavage site duplex. To evaluate the extent to which the proposed cleavage-site duplex (stem I) might contribute to substrate binding, the effect of varying substrate size was examined. DHS1 was 5' end-labeled with $^{32}$P, gel purified and then subjected to partial hydrolysis to generate a ladder of end-labeled fragments when displayed on a sequencing gel. Incubation of the mixture of end-labeled fragments with excess ADC1 in 10 mM Mg$^{2+}$ resulted in cleavage of the fragments which were 10 nt or longer (see FIG. 4A, lanes 9 and 10), indicating that at least 7 nt 3' to the cleavage site were required under these conditions. Raising the Mg$^{2+}$ concentration to 50 mM did not reduce the size requirement, but lowering the Mg$^{2+}$ concentration to 2 mM (lanes 7 and 8) or adding urea to 2M (lanes 11 and 12) reduced activity. This experiment identified those substrate fragments which were cleaved rapidly; it would not reveal a low level of cleavage of the smaller fragments. However, because the experiment was done in enzyme excess, it is unlikely that the shorter fragments were simply competed from the binding site by the longer fragments, and therefore it should present a fairly accurate picture of the requirements 3' to the cleavage site.

The requirements 5' to the cleavage site were examined in a similar manner; a 10 nt long substrate, DHS2, was 3' end labeled with [5'-$^{32}$P]pCp and the analysis repeated (see FIG. 4B). The labeled substrate (5' UUC^GGGUCGGp*Cp (SEQ ID No. 1), where p* is the labeled phosphate) contained 8 nt 3' to the cleavage site, and in the presence of $Mg^{2+}$, substrates which were 9 nt or longer were cleaved by ADC1 to generate an 8 nt long labeled product (lanes 7–9). These data indicate that a single nucleotide 5' to the cleavage site is sufficient for substrate binding and cleavage. This is consistent with the finding with the genomic self-cleaving sequence which demonstrated that one nucleotide 5' to the cleavage site is sufficient for self-cleavage.

Octanucleotides of the sequence 5' N^GGGUCGG, where N was either riboC, U, A, G, or deoxyC, were 5' end-labeled with $^{32}$P and tested for cleavage by ADC1. Release of [5'-$^{32}$P]nucleoside 5' phosphate 2',3' cyclic phosphate was monitored by thin layer chromatography (see FIG. 5A). Oligonucleotides with 5' rC, rU and rA were cleaved at similar rates and to similar extents under the conditions tested (see FIG. 5B). The oligonucleotide with rG was cleaved less efficiently, approximately 10 fold slower, even when four fold higher enzyme concentrations were used (see FIG. 5B). With a deoxyribose at the −1 position, no cleavage was detected (see FIG. 5A).

For the HDV-derived enzyme and substrates used in this example, the data indicate a target size of 7–8 nt under the conditions tested. The data indicate that specificity is strongly influenced by Watson-Crick base-pairing between the substrate and the enzyme.

Evidence for basepairing at two positions within the cleavage site duplex (positions 3 with 37, and 4 with 36) has been presented (FIGS. 1 & 2). The results with the trans reaction are consistent with those obtained by mutagenesis of the equivalent positions in the self-cleaving RNA. The potential for a GU basepair (1G:39U) at the base of the duplex is suggested; mutations at either position reduced self-cleavage activity and substitutions that might generate Watson-Crick basepairs do not restore full self-cleavage activity. For either the antigenomic sequence (FIG. 1A) or the genomic sequence, in which there is a U at position −1, it is possible to extend stem I to include a base-pair (CG or UG, see FIG. 1G) involving the nt at position −1 and a G at position 40. Results from the trans reaction indicate that only a G at position −1 substantially decreased cleavage. These data were consistent with results obtained from mutagenesis of the self-cleaving form of the RNA, in which a G at the −1 position also resulted in slow cleavage.

The trans reaction was used to test a prediction of the model for the mechanism of cleavage. Self-cleavage of HDV RNA generates a 2',3'-cyclic phosphate and a 5' OH, suggesting that cleavage occurs by a transesterification mechanism, involving attack on the phosphorous at the cleavage site by the adjacent 2' OH or O⁻. If that mechanism is correct, it predicts that removal of the hydroxyl group from that 2' position will prevent cleavage. The lack of cleavage of the substrate missing the 2' hydroxyl group therefore provides additional evidence for the transesterification mechanism.

EXAMPLE 2

Circular RNA Enzymes

A method by which almost any short sequence of RNA can be converted to a circular form in vitro or, potentially, in vivo is described below. This technology is useful for producing small circular forms of enzymatic RNAs that are designed to cleave substrate RNAs at specific sequences. The specificity of enzymes for the substrate RNA is mainly determined by basepairing with the target sequence and therefore can be easily manipulated. In addition to the demonstrated use of enzymes as a tool in molecular biology (to cleave RNA in vitro), such enzymes provide an alternative to antisense RNA/DNA as therapeutics or as a means to modulate gene expression. The important advantage over antisense technology is that the enzymes act catalytically.

Cleavage of RNA by engineered enzymes can be very efficient in vitro. The ability of enzymes to affect levels of target RNAs in cells looks promising but there are several obstacles to overcome. Some of those obstacles are: (i) the introduction and expression of the enzymes in the cell, (ii) the stabilization of the enzyme against degradative processes in the cell, and (iii) increasing the probability that the RNA folds into an active conformation.

While these obstacles can be overcome by those in the art to some extent, circular enzymes offer better solutions to these obstacles. For example, the circular enzymes can be synthesized in vitro or expressed in vivo as part of a larger transcript. However, once excised and converted to a circle, it is not burdened either by sequences required for expression or by polyadenylation, both of which can interfere with the folding of the RNA into the enzyme conformation. The circular form of RNA will also be resistant to exonucleolytic degradation and therefore have a longer half-life in vivo. From a structural standpoint, a circular RNA will be constrained in terms of folding options, and therefore, it is possible to design it to fold into the active form more efficiently than a linear enzyme.

In the studies discussed below there is shown technology that generates circular RNA efficiently (using a second catalytic RNA), a discussion of the design and synthesis of circular enzymes, and characterization of the catalytic activity and structure of those enzymes. While the discussion focuses on in vitro studies, these can be extended readily to in vivo systems.

Basically, intramolecular reaction of a self-splicing RNA can be used to yield a circular (C) exon. The generation of the C RNA results from rearranging intron and exon sequences (the exon sequences can be essentially anything) such that a single exon is sandwiched between intron domains that have been permuted (see FIG. 11). The resulting RNA transcript has the normal 5' splice site 3' of the normal 3' splice site. Upon splicing, the ends of the (single) exon are joined and it is released as a circle. The circle is generated because the positions of the splice sites have been reversed.

To examine folding possibilities of group I introns, several versions of the permuted intron have been made (FIG. 11) and all generate the circular exon diagnostic for in vitro splicing activity (by a method shown generally in FIG. 12). The production of circles indicated that the splicing reaction occurred. As is clear from FIGS. 11 and 12, the Tetrahymena group I intron sequence can be used to provide a permuted intron with only minor modifications. The exon portion, which will contain the enzyme sequences, is engineered to contain convenient restriction endonuclease sites to facilitate the introduction of enzyme sequences. As new constructs are made, the efficiency of circle production is monitored to optimize conditions. Specific changes which are known to enhance splicing activity in vitro are incorporated and tested.

Sequences based on the HDV RNA enzyme, "hammerhead", or the "hairpin" motifs of self-cleaving RNA are synthesized and inserted into the permuted intron. Circular forms are generated in vitro and can be tested against appropriate target and control substrates. Enzyme and target sequences can be adapted from those already shown to work with linear (L) forms of the ribozymes. Circularly permuted HDV enzymes are active. One example is shown in FIG. 9. Results show that a circular RNA enzyme will be active.

To make a permuted intron sequence (based on normal intron sequence) a DNA fragment containing the Tetrahymena intron (413 basepairs) and flanking sequences (~60 basepairs) was ligated under dilute conditions to generate a circular form of the sequence. This DNA was then cut with one of three restriction endonucleases to cleave in non-essential regions of the intron sequence, generating a linear fragment of DNA in which the exon sequence was flanked by intron sequences. The DNA was cloned into a plasmid downstream of a T7 promoter to facilitate production of large amounts of RNA. RNA produced from all three versions of this construct generated C exons under splicing conditions.

To make permuted intron sequences suitable for introducing enzyme sequences the above procedure is varied slightly. Oligonucleotide primers are synthesized to contain several unique restriction sites along with sequences complimentary to the two ends of the intron containing fragment. The polymerase chain reaction (PCR) is used to amplify the intron sequence and essential exon sequences. The resulting PCR product is then purified and circularized. Blunt-end ligation can be used, but it is also useful to incorporate a common restriction site near both ends which can be cleaved prior to circularization. The circle is recleaved as described above, ligated into a vector containing a T7 promoter, and miniprep DNA screened by restriction endonuclease digestion for proper orientation of the fragment. The entire intron-exon sequence can be sequenced to insure that no errors were generated by the PCR reaction. Generally, the exon/cloning site sequence is about 40 basepairs in length.

These plasmids are used as cloning vectors for fragments containing sequences to be transcribed and converted to circles.

Circle production can be optimized for each sequence examined. In general, self-splicing occurs under a wide variety of conditions: 5–50 mM $Mg^{2+}$, 30°–50° C., 0–200 mM monovalent salt, and pH 7–9. The reaction will tolerate low concentrations of denaturants (urea and formamide) and in some cases specificity can be enhanced in their presence. The effect of varying these conditions is examined to determine optimum conditions.

Circles of RNA are readily detected by polyacrylamide gel electrophoresis under denaturing conditions (7M urea). Generally, C forms are distinguished from L forms of nucleic acid by varying some condition in the gel (acrylamide concentration, extent of crosslinking, ionic strength, urea concentration, possibly temperature) and detecting a band with an anomalous mobility shift. The easiest method is to run two gels with 8% and 12% polyacrylamide (the size of the circle will determine the actual optimal concentrations, but this works well for circles of about 60 nt). Alternatively, a sample can be analyzed in two dimensions (low percentage gel followed by a second dimension at higher percentage) where circles will run off the diagonal. This technique is not necessary unless the mixture of products is complex and the circle co-migrates with linear species under both sets of conditions.

The simplest way to demonstrate that an isolated species of RNA is circular is to subject it to partial hydrolysis (or enzymatic nicking), and then rerun it in a gel system which will separate the C form from the L form. A circular RNA which is nicked once will display a discrete shift in the mobility of the product, whereas a linear species would form a smear of smaller fragments. Radiolabeled RNA is used to quantify the kinetics and extent of circle production. In the absence of a radioimager, bands located by autoradiography are excised and counted in a scintillation counter.

Removal of non-essential sequences from the intron portion of the permuted sequence facilitates proper folding by limiting the stable folding options. Correct folding also is facilitated by replacing non-essential loop sequences at the ends of essential stems with "super-loops". Such loop sequences at the ends of stems confer greater than usual stability.

The most well characterized small enzymes have been derived from the self-cleaving RNAs of the hammerhead motif. Although the following description is for the hammerhead based enzyme, similar work can be performed with the hairpin based enzyme or HDV-based enzymes, and related enzymes. The basic idea is to assemble a self-cleaving RNA (normally a single strand of RNA) from two strands of RNA such that the one which is cleaved is the substrate and the other the enzyme.

Synthetic duplex DNA fragments containing the sequences corresponding to previously characterized enzymes, are synthesized and inserted into the permuted intron constructs described above to generate circles. Alternatively, they are inserted directly downstream of a T7 promoter to generate L-forms of the enzyme. The resulting plasmid DNA is cleaved with an appropriate restriction endonuclease, and runoff transcripts made by in vitro transcription with T7 RNA polymerase. With the permuted intron constructs, some splicing and hence some circle production will occur during the course of the transcription reaction; however, following transcription the conditions are adjusted to splice the remaining unspliced material. The enzymes are then purified by polyacrylamide gel electrophoresis under denaturing conditions.

Substrates for the enzymes are also generated by in vitro transcription. Short oligonucleotides are often used in these assays. The C and L versions of the enzymes are tested for cleavage activity against a common substrate RNA. To control for possible aggregation of the RNAs the enzyme and substrate RNA are heated separately to 95° C. in Tris buffer (pH 7.5) in the absence of $Mg^{2+}$ for 1 minute, cooled to the reaction temperature, $MgCl_2$ is added, and then preincubated at the reaction temperature for 15 minutes prior to mixing. The reaction is terminated by the addition of EDTA and denaturant, and the products fractionated on a polyacrylamide gel in 7M urea. The specific activity of the C enzyme is compared to the L enzyme under conditions where the amount of cutting increases with increasing L enzyme.

EXAMPLE 3

Cutting Duplex RNA

Referring to FIG. 10, the site of cleavage in the self-cleaving structure is located at the base of stem I, and cleavage occurs 5' to the G of the G-U basepair. Rather than including the 3' side of stem I in the enzyme and requiring it to base-pair with a single-stranded RNA substrate (the 5' side of stem I), a form of the enzyme can be generated (see, FIG. 10) which omits stem I entirely. This form of the enzyme associates with the duplex through tertiary contacts to form a cleavable structure.

Mutations at each of the G nucleotides in the sequence connecting stems I and IV are important for full activity, therefore the 5' end of the enzyme should start at, or at least include, the G at position 40 in the antigenomic sequence (or the equivalent G in the genomic sequence). Stem III is also important for full activity, so the 3' end of the enzyme should include all of stem III and loop III. Stem IV can be shortened and both stems II and IV closed with loops. The loop at the end of stem III and the sequence connecting stems IV and II will not tolerate drastic changes so they should also be left intact.

This is the first description of use of a modified self-cleaving ribozyme, e.g., HDV, hammerheads and hairpins (rather than self-splicing ribozymes), to cleave double stranded RNA. Szostak, 311 *Nature* 83, 1986 describe a version of the self-splicing Tetrahymena intron lacking stem I that will cleave a duplex, in a guanosine dependent reaction, at a position 3' to the U in a U-G base pair. This differs from the present invention, since the present enzymes cleave a different strand, and do not require guanosine. Also, the HDV-derived enzymes are much smaller and thus more useful.

Uses

The enzymatic RNA of this invention are useful therapeutically and for diagnostic procedures well recognized in the art. Because of their small size and target sequence of 7–8 nucleotides, these molecules are useful in vivo for cleaving specific target molecules. The RNA may be introduced by any standard procedures, including direct administration to a patient in a therapeutic amount within a pharmaceutical medium, or even by transfection of a virus which causes production of the RNA in vivo. In diagnosis, the presence of a particular RNA sequence can be readily demonstrated, as in the examples shown above and as discussed in Cech et al., supra.

Other embodiments are within the following claims.

What is claimed is:

1. A circular ribonucleic acid molecule lacking an ability to inter-convert between linear and circular forms, wherein said circular ribonucleic acid molecule has enzymatic activity to cleave a separate RNA molecule at a cleavage site.

2. A method for forming a circular ribonucleic acid lacking the ability to interconvert between linear and circular forms comprising the steps of:

incubating a self-cleaving and self-ligating ribonucleic acid molecule which forms said circular ribonucleic acid under self-cleaving and self-ligating conditions thereby generating said circular ribonucleic acid molecule.

3. The method of claim 2, wherein said circular ribonucleic acid molecule is an enzymatic fibonucleic acid molecule.

4. The method of claim 2, wherein said self-cleaving and self-ligating ribonucleic acid molecule is derived from a group I intron.

5. The method of claim 2, wherein said self-cleaving and self-ligating ribonucleic acid molecule is derived from a group II intron.

* * * * *

UNITED STATES PATENT AND TRADEMARK OFFICE
CERTIFICATE OF CORRECTION

PATENT NO. : 5,712,128
DATED : January 27, 1998
INVENTOR(S) : Michael D. Been et al.

It is certified that error appears in the above-identified patent and that said Letters Patent is hereby corrected as shown below:

Column 24, Line 19: delete "fibonucleic" and insert --ribonucleic--

Signed and Sealed this

Sixteenth Day of March, 1999

Attest:

Q. TODD DICKINSON

Attesting Officer

Acting Commissioner of Patents and Trademarks